United States Patent
Koch et al.

(10) Patent No.: US 8,080,393 B2
(45) Date of Patent: Dec. 20, 2011

(54) METHODS FOR PRODUCTION OF OLIGONUCLEOTIDES

(75) Inventors: Jorn Erland Koch, Ry (DK); Magnus Stougaard, Aarhus C (DK); Jakob Schwalbe Lohmann, Ry (DK)

(73) Assignee: Olink AB, Uppsala (SE)

( * ) Notice: Subject to any disclaimer, the term of this patent is extended or adjusted under 35 U.S.C. 154(b) by 697 days.

(21) Appl. No.: 11/911,521

(22) PCT Filed: Apr. 10, 2006

(86) PCT No.: PCT/DK2006/050012
§ 371 (c)(1),
(2), (4) Date: Jun. 23, 2008

(87) PCT Pub. No.: WO2006/108423
PCT Pub. Date: Oct. 19, 2006

(65) Prior Publication Data
US 2010/0028953 A1    Feb. 4, 2010

(30) Foreign Application Priority Data
Apr. 12, 2005    (DK) .................... 2005 00521

(51) Int. Cl.
*C12P 19/34* (2006.01)
*C07H 21/02* (2006.01)
(52) U.S. Cl. ..................... 435/91.2; 536/23.1
(58) Field of Classification Search .......... None
See application file for complete search history.

(56) References Cited

U.S. PATENT DOCUMENTS

| | | | |
|---|---|---|---|
| 4,683,195 A | 7/1987 | Mullis et al. | 435/6 |
| 4,683,202 A | 7/1987 | Mullis | 435/91 |
| 4,800,159 A | 1/1989 | Mullis et al. | 435/172.3 |
| 5,354,668 A | 10/1994 | Auerbach | 435/91.1 |
| 5,591,609 A | 1/1997 | Auerbach | 435/91.2 |
| 5,614,389 A | 3/1997 | Auerbach | 435/91.2 |
| 5,648,245 A | 7/1997 | Fire et al. | 435/91.1 |
| 5,714,320 A | 2/1998 | Kool | 435/6 |
| 5,733,733 A | 3/1998 | Auerbach | 435/6 |
| 5,834,202 A | 11/1998 | Auerbach | 435/6 |
| 5,854,033 A | 12/1998 | Lizardi | 435/91.2 |
| 5,876,924 A | 3/1999 | Zhang et al. | 435/5 |
| 5,942,391 A | 8/1999 | Zhang et al. | 435/6 |

(Continued)

FOREIGN PATENT DOCUMENTS

EP    0 497 272 B1    8/1992
(Continued)

OTHER PUBLICATIONS

Alsmadi, et al, "High accuracy genotyping directly from genomic DNA using a rolling circle amplification based assay", *BMC Genomics* 2003, 4, pp. 1-18.

(Continued)

*Primary Examiner* — Samuel Woolwine
(74) *Attorney, Agent, or Firm* — Sunstein Kann Murphy & Timbers LLP

(57) ABSTRACT

The present invention relates to production of oligonucleotides using rolling circle replication, wherein synthesised multimeric oligonucleotides are reduced to mononucleotides using a nicking cassette. Thus, the invention provides a method for the production of oligonucleotides, enabling efficient amplification of oligonucleotides at lengths up to at least 1000 nucleotides and in high amounts contained within a nicking cassette.

41 Claims, 5 Drawing Sheets

U.S. PATENT DOCUMENTS

Figure 1:
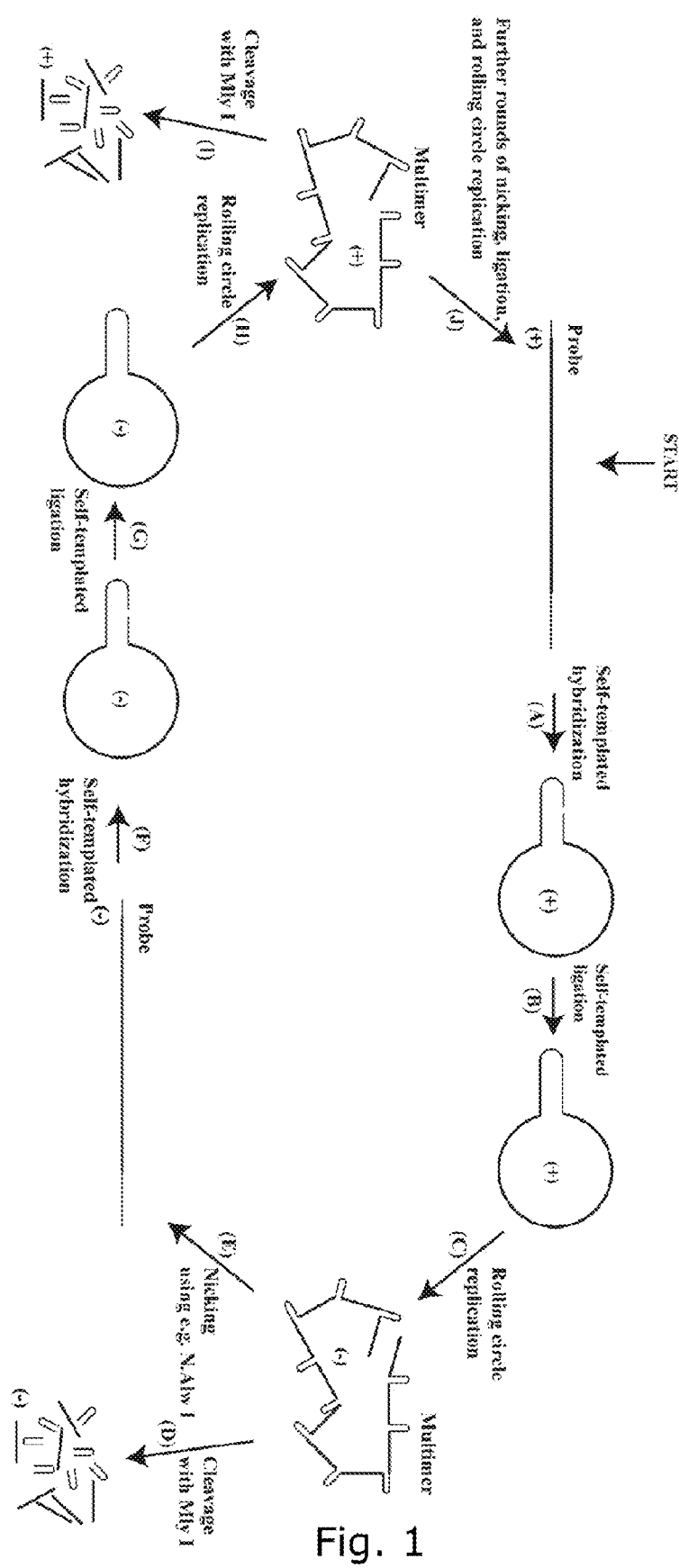

| | | | | |
|---|---|---|---|---|
| 6,077,668 | A | 6/2000 | Kool | 435/6 |
| 6,096,880 | A | 8/2000 | Kool | 536/25.3 |
| 6,143,495 | A | 11/2000 | Lizardi et al. | 435/6 |
| 6,183,960 | B1 | 2/2001 | Lizardi | 435/6 |
| 6,210,884 | B1 | 4/2001 | Lizardi | 435/6 |
| 6,218,152 | B1 | 4/2001 | Auerbach | 435/91.2 |
| 6,221,603 | B1 | 4/2001 | Mahtani | 435/6 |
| 6,261,808 | B1 | 7/2001 | Auerbach | 435/91.1 |
| 6,329,150 | B1 | 12/2001 | Lizardi et al. | 435/6 |
| 6,344,329 | B1 | 2/2002 | Lizardi | 435/6 |
| 6,368,802 | B1 | 4/2002 | Kool | 435/6 |
| 6,448,017 | B1 | 9/2002 | Auerbach | 435/6 |
| 6,569,647 | B1 | 5/2003 | Zhang et al. | 435/91.2 |
| 6,632,609 | B2 | 10/2003 | Lizardi | 435/6 |
| RE38,442 | E | 2/2004 | Zhang et al. | 435/5 |
| 6,740,745 | B2 | 5/2004 | Auerbach | 536/23.1 |
| 6,797,474 | B2 | 9/2004 | Lizardi | 435/6 |
| 6,855,523 | B2 | 2/2005 | Zhang et al. | 435/91.2 |
| 2003/0087241 | A1 | 5/2003 | Kool | 435/6 |
| 2004/0086892 | A1 | 5/2004 | Crothers et al. | 435/6 |
| 2005/0069929 | A1* | 3/2005 | Chestnut et al. | 435/6 |
| 2005/0069938 | A1 | 3/2005 | Wang et al. | 435/6 |
| 2008/0044862 | A1* | 2/2008 | Schatz et al. | 435/85 |

FOREIGN PATENT DOCUMENTS

| | | |
|---|---|---|
| EP | 0 500 224 A2 | 8/1992 |
| EP | 0 543 612 B1 | 5/1993 |
| EP | 0 807 186 B1 | 11/1997 |
| EP | 0 862 656 B1 | 9/1998 |
| EP | 0 915 991 B1 | 5/1999 |
| EP | 0 971 039 A2 | 1/2000 |
| JP | 04262799 A | 9/1992 |
| JP | 04304900 A | 10/1992 |
| WO | WO 92/01813 | 2/1992 |
| WO | WO 93/04198 | 3/1993 |
| WO | WO 93/09245 | 5/1993 |
| WO | WO 94/03630 | 2/1994 |
| WO | WO 95/35390 | 12/1995 |
| WO | WO 97/19193 | 5/1997 |
| WO | WO 97/20948 | 6/1997 |
| WO | WO 98/38300 | 9/1998 |
| WO | WO 99/49079 | 9/1999 |
| WO | WO 00/77250 A2 | 12/2000 |
| WO | WO 01/77383 A2 | 10/2001 |
| WO | WO 02/50310 A2 | 6/2002 |
| WO | WO 03/044193 A2 | 5/2003 |
| WO | WO 2004/050915 A1 | 6/2004 |
| WO | WO 2004/059005 A2 | 7/2004 |
| WO | WO 2005/001063 A2 | 1/2005 |

OTHER PUBLICATIONS

Larsson, et al., In situ genotyping individual DNA molecules by target-primed rolling-circle amplification of padlock probes, *Nature Methods*, vol. 1, No. 3, pp. 227-232, Dec. 2004.

Dahl, et al., "Circle-to-circle amplification for precise and sensitive DNA analysis", *PNAS*, vol. 101, No. 13, pp. 4548-4553, Mar. 30, 2004.

Fire and Xu, "Rolling replication of short DNA circles", *Proc. Natl. Acad. Sci. USA* 92, pp. 4641-4645, May 1995.

White, et al., "Concatemer Chain Reaction: A Taq DNA Polymerase-Mediated Mechanism for Generating Long Tandemly Repetitive DNA Sequences", *Analytical Biochemistry 199*, pp. 184-190, (1991).

Ijdo, et al., "Improved telomere detection using a telomere repeat probe (TAGGG), generated by PCR", *Nucleic Acids Research*, vol. 19, No. 17, p. 4780, Apr. 30, 1991.

Koch, et al., "Oligonucleotide-priming methods for the chromosome-specific labelling of alpha satellite DNA in situ", *Chromosoma (Berl)* (1989) (98:259-265).

Andersen, et al., "Active, but not inactive, human centromeres display topoisornerase II activity in vivo", *Chromosome Research* 10, 305-312, 2002.

Kerem, et al., "In situ nick-translation distinguishes between active and inactive X chromosomes", *Nature*, 304, 88-90 (Jul. 7, 1983), Abstract only.

Kerem, et al., "Mapping of DNAase I Sensitive Regions on Mitotic Chromosomes", *Cell*, vol. 38, 493-499, Sep. 1984.

Jablonka, et al., "DNA hypomethylation causes an increase in DNAase-I sensitivity and an advance in the time of replication of the entire inactive X chromosome", *Chromosoma* (Berl) (1985) 93:152-156.

Nose, et al., "Detection of Carcinogen-Induced DNA Breaks by Nick Translation in Permeable Cells", *Biochemical and Biophysical Research Communications*, vol. 111, No. 2, pp. 383-389, 1983.

Filipkowski, et al., "DNA fragmentation in rat brain after intraperitoneal administration of kainate", *NeuroReport*, vol. 5(12), 1538-1540 Jul. 1994, Abstract only.

Zettl, et al., "Apoptotic cell death of T-lymphocytes in experimental autoimmune neuritis of the Lewis rat", *Neuroscience Letters*, 176 (1994) 75-79.

Gold, et al., "Differentiation between cellular apoptosis and necrosis by the combined use of in situ tailing and nick translation techniques", *Lab Invest*. Aug. 1994;71(2):219-25, Abstract only.

Luchniak, et al., "Different DNA methylation in A and B chromosomes of Crepis capillaries detected by in situ nick-translation. Comparison with molecular methods", *Folia Histochem Cytobiol*, 2002;40(3):325-30, Abstract only.

Andersen, et al., "CpG islands detected by self-primed in situ labeling (SPRINS)", *Chromosoma* (1998) 107:260-266.

Wu and Wallace, "The Ligation Amplification Reaction (LAR)—Amplification of specific DNA Sequences Using Sequential Rounds of Template-Dependent Ligation", *Genomics 4*, 560-569 (1989).

Kalin, et al., "Evaluation of the ligase chain reaction (LCR) for the detection of point mutations", *Mutat Res*. Oct. 1992;283(2):119-23, Abstract only.

Nilsson, et al., "Padlock Probes: Circularizing Oligonucleotides for Localized DNA Detection", *Science*, New Series, vol. 265, No. 5181, Genome Issue, (Sep. 30, 1994), pp. 2085-2088.

Nilsson et al., "Padlock probes reveal single-nucleotide differences, parent of origin and in situ distribution of centromeric sequences in human chromosomes 13 and 21", *Nature Genetics*, vol. 16, pp. 252-255, Jul. 1997.

Nilsson, et al., "Making Ends Meet in Genetic Analysis Using Padlock Probes", *Human Mutation* 19:410-415 (2002).

Gazit, et al., "Active Genes are Sensitive to Deoxyribonuclease I During Metaphase", *Science*, vol. 217, Aug. 13, 1982, pp. 648-650.

European Patent Office, Official Communication dated Mar. 13, 2009; Application No. 06 706 145.7-1222 (English abstract).

* cited by examiner

A  ---(N)n---5'-YY-CCTCAGC-YY-AATAA-XX-GCTGAGG-XX-3'---(N)n---

(SEQ ID No:25)

B  ---(N)n---5'-YY-GCTGAGG-YY-AATAA-XX-CCTCAGC-XX-3'---(N)n---

(SEQ ID No:26)

C  ---(N)n---5'-YY-GGATCYYYYY-YY-AATAA-XX-XXXXXGATCC-XX-3'---(N)n---

(SEQ ID No:27)

D  ---(N)n---5'-XX-GAATGCX-X-AATAA-Y-YGCATTG-YY-3'---(N)n---

(SEQ ID No:47)

A
----(N)n---5'-GGATC-GACTC-AA-AATAA-TT-GAGTC-GATCC-3'---(N)n----

(SEQ ID No: 6)

B
----(N)n---5'-GGATC-GACTC-YY-AATAA-XX-GAGTC-GATCC-3'---(N)n----

(SEQ ID No: 40)

C
----(N)n---5'-GGATC-GACTC-GCTGAGG-AA-AATAA-TT-CCTCAGC-GAGTC-GATCC-3'---(N)n----

(SEQ ID No: 7)

D
----(N)n---5'-YYYYY-GACTC-GCTGAGG-YY-AATAA-XX-CCTCAGC-GAGTC-XXXXX-3'---(N)n----

(SEQ ID No: 48)

METHODS FOR PRODUCTION OF OLIGONUCLEOTIDES

FIELD OF THE INVENTION

The present invention represents an improved method for the production of oligonucleotides. The invention also relates to probes for use in the method.

BACKGROUND OF THE INVENTION

In combination with sequencing of genomes, automated DNA synthesizers have given researchers the possibility to acquire almost any genetic element as an oligonucleotide and, at least for short oligonucleotides, at a fairly low cost. Two current limitations relate to: I) The production of large amounts of high quality oligonucleotides and II) The synthesis of very long oligonucleotides (200-1000 nucleotides). Concerning the former issue, the quality of the oligonucleotides can be affected by factors related to the chemical synthesis method, including depurination and dG to dA transitions. The maximum length of the synthesized oligonucleotides is currently around 150 nucleotides, with the yield and quality dropping as the length increases.

The main current uses of oligonucleotides are as primers for the polymerase chain reaction (PCR), for reverse transcription PCR (rtPCR), for sequencing, and as substrates for different enzymatic reactions. In recent years, new techniques have appeared which demand high quality, 5' phosphorylated oligonucleotides of 70-100 nucleotides in length (e.g. padlock probes). Such probes may well cost 100-200$, taking the extra cost for 5' phosphorylations (25-35$) and HPLC purifications (25-35$) into account.

These oligonucleotides can to some extent be amplified enzymatically by known methods, e.g. cloning, PCR, rolling circle amplification or Circle-to-circle amplification (C2CA). However, all of these techniques have limitations.

Cloning

Cloning is a time consuming technique where a double stranded DNA sequence is inserted into a plasmid, transformed into an appropriate host organism e.g. bacteria or yeast, the organism grown, and the DNA purified. This is then followed by isolation of the DNA fragment of interest by restriction endonucleases. The technique is laborious, is more suitable for the production of double stranded DNA and at the same time a lot of non-useful DNA is co-amplified and, in particular for the production of shorter DNA segments, the production of non-useful (vector)-DNA will be dominant. Furthermore a laboratory classified for gene modified organisms is required.

PCR

PCR is based on the amplification of a double stranded DNA fragment by the use of a thermostable DNA polymerase and primers complementary to the DNA fragment. Amplification of the DNA fragment takes place by alternating heating and cooling. This technique is more suitable for the production of double stranded DNA and requires a primer for each amplified DNA strand. Furthermore, since the product created is used as template for the next rounds of amplification, mis-incorporation of a nucleotide early in the process will be amplified exponentially along with the desired product.

Rolling Circle Replication

In vitro rolling circle replication traditionally uses a circular single stranded DNA oligonucleotide as a rolling-circle-template and a short oligonucleotide as a primer. The addition of a DNA polymerase and dNTPs starts the polymerization. As the rolling-circle-template is endless, the product will be a long single stranded DNA molecule composed of tandem repeats complementary to the rolling-circle-template. In contrast to the PCR reaction, a falsely incorporated nucleotide will not be further amplified as the circular oligonucleotide is template for each round of amplification.

US 2003/0087241 describes the method of "Rolling circle amplification" in which a rolling circle product can be designed in a way, that allows it to fold into distinct hairpin structures containing a binding site for a restriction endonuclease. The rolling circle product can therefore, by a restriction endonuclease, be turned into monomers. Limitations to this technique include that it does not amplify the circular oligonucleotide, but rather replicate the complementary sequence, and that it only provides one round of amplification.

Circle-to-Circle Amplification

Circle-to-circle amplification (C2CA) is a method for the amplification of a single stranded DNA sequence, based on successive rounds of rolling circle DNA synthesis. The DNA sequence is circularized using an external template for ligation. Following rolling circle DNA synthesis, a long tandem repeat complementary to the start DNA sequence is synthesized. By hybridization of an oligonucleotide to the rolling circle product, at a position containing a restriction site, the single stranded tandem repeat can be turned into monomers by addition of a restriction endonuclease. Following a second circularization, rolling circle DNA synthesis, hybridization of a new oligonucleotide (complementary to the first one) and cutting with a restriction endonuclease, an amplification of the start DNA sequence has taken place through two rounds of rolling circle DNA synthesis (Dahl F et al., Proc Natl Acad Sci USA. 101(13), 4548-53 (2004)).

This technique requires the additional production of oligonucleotides for cleavage of the rolling circle product, and, even more importantly, it does not provide free design of the ends of the DNA sequence to be amplified as they are defined by the presence of a binding/cleavage site for a restriction endonuclease.

Taken together, there is a need for improved techniques for the production of large quantities of high-quality oligonucleotides to eliminate the limitations associated with the existing techniques as outlined above. The invention disclosed here represents just that, providing large quantities of phosphorylated high quality oligonucleotides, e.g. exhibiting superior performance for circle formation.

SUMMARY OF THE INVENTION

In one aspect of the invention, the invention provides a method for the production of oligonucleotides, enabling efficient amplification of oligonucleotides at lengths up to at least 1000 nucleotides and in high amounts contained within a nicking cassette. The reaction principle applies the alternating strand approach of the circle-to-circle amplification, but adding a nicking cassette to the sequence of the oligonucleotide to be amplified. This nicking cassette is capable of forming a double stranded structure (a hairpin) comprising one or more nicking sites. The one or more nicking sites allow the first rolling circle product to be cleaved into monomers.

The double stranded feature of the nicking cassette allows the nicking to be done without the addition of an extra oligonucleotide to form the proper double stranded substrate for the nicking enzyme. This feature also enables the monomers released from a rolling circle product by the nicking enzyme to be circularized without the addition of external ligation templates. The design thus eliminates the need for cleavage and ligation of oligonucleotides inherent to the circle-tocircle-amplification technique. The monomers produced in the first round of amplification are then, upon circularisation, subjected to a second round of amplification. If desired, the nicking enzyme may be employed again and the amplification reaction repeated. Thus, this aspect of the invention provides production of oligonucleotides contained within a nicking cassette, at any length, at least within the range 10-1000 nucleotides, and in amounts that are largely limited by the number of successive rounds of ligation, rolling circle replication, and nicking.

In more detail, the method is based on the use of a nucleic acid probe (probe (A)), comprising the sequence of the oligonucleotide to be amplified and a nicking cassette. The nicking cassette is a nucleic acid sequence comprising complementary sequences enabling the nicking cassette to hybridise to itself, and further comprising a site for a nicking enzyme. The probe (probe (A)) is circularised either by self-templated ligation via hybridisation of the complementary regions of the nicking cassette, or by externally templated ligation of one or more oligonucleotides. Upon circularisation, the probe (probe (A)) is used as rolling-circle-template for rolling circle replication, employing a primer recognizing part of the probe. The rolling circle product, comprising multiple copies of the complementary sequence to the probe (A) (probe (B)), is exposed to a nicking enzyme, which cuts within the nicking cassette. This results in multiple copies of probe (B).

Upon nicking, circularisation of probe (B) is mediated by self-templated ligation via hybridisation of the complementary regions of the nicking cassette. The multiple copies of the circularized probe (B) are used for rolling circle replication employing primers with a target sequence complementary to part of probe (B). In the following step a second nicking reaction is employed. In this way, the method of the invention provides production of an oligonucleotide up to a length of at least 1000 nucleotides in high amounts contained within a nicking cassette.

Successive rounds of ligation, rolling circle replication, and nicking can be performed, thereby amplifying probe (A) and probe (B) further. It is to be understood that amplified products of both probe (A) and probe (B) can be obtained by the method of the invention.

In a second aspect of the invention, the invention provides a method for the production of oligonucleotides, enabling efficient amplification of oligonucleotides at lengths up to about 1000 nucleotides and in high amounts. The reaction principle applies the alternating strand and self-templated approach outlined above, but adding a restriction site to the nicking cassette. In the following section a nicking cassette comprising one or more nicking sites and one or more restriction sites will be referred to as a nicking cassette or a suicide cassette, alternatively, depending upon its use.

This suicide cassette is capable of forming a double stranded structure (a hairpin) comprising one or more nicking sites and one or more restriction sites. The one or more nicking sites allow the first, and any subsequent, rolling circle products to be cleaved into monomers as described above.

The one or more restriction sites allow the rolling circle products to be converted into multiple copies of the oligonucleotide to be amplified contemporary with the release of the suicide cassette from the oligonucleotides. Thus, the method of the invention provides production of oligonucleotides with freely designable 5'-ends and 3'-ends, at any lengths, at least within the range of 10-1000 nucleotides, and in amounts that are largely limited by the number of rounds of ligation, rolling circle replication and nicking.

In more detail, the method provides alternating amplification of probe (B) from probe (A) and of probe (A) of probe (B) as outlined above, with the added feature that any of the rolling circle products may be digested with the restriction enzyme releasing the suicide cassette from the oligonucleotide.

Thus, in one aspect of the invention, the invention relates to a method for amplifying an oligonucleotide contained within a nicking cassette through successive rounds of ligation, rolling circle replication, and nicking:

A method for amplifying one or more oligonucleotides comprising
 a) creating a nucleic acid probe (A) comprising one or more oligonucleotides and one or more nicking cassettes, and
 b) circularising of the probe (A), and
 c) providing a primer with a target sequence in part of said probe (A), and
 d) effecting rolling circle replication of said probe (A), and
 e) nicking of the rolling circle product of probe (A) within the one or more nicking cassettes obtaining multiple copies of a probe (B) complementary to the probe (A),
 f) circularising of the probe (B), and
 g) providing a primer with a target sequence in part of said probe (B), and
 h) effecting rolling circle replication of said probe (B), and
 i) nicking of the rolling circle product of probe (B) within the one or more nicking cassettes obtaining multiple copies of a probe (A) complementary to the probe (B).

The invention also relates to a probe for use in the method as outlined above. The probe of the invention comprises a nicking cassette, wherein the nicking cassette is a nucleic acid sequence comprising complementary sequences, enabling the nicking cassette to hybridise to itself and bind the necessary modifying enzymes.

In a second aspect of the invention, the invention relates to a method for amplifying an oligonucleotide contained within a suicide cassette, releasing the oligonucleotide from the suicide cassette at the end of the amplification.

The aspect also relates to a probe for use in the method as outlined above. The probe of the invention comprises a suicide cassette, wherein the suicide cassette is a nucleic acid sequence comprising complementary sequences, enabling the suicide cassette to hybridise to itself, bind the necessary modifying enzymes, and be cleaved out at the end of the reaction.

Taken together, in one aspect the invention relates to a method for the amplification of one or more oligonucleotides contained within a nicking cassette comprising one or more binding and cleavage sites for nicking enzymes. In a second aspect the nicking cassette is further equipped with one or more restriction sites (giving rise to a so-called suicide cassette) allowing the release of the cassette from the one or more oligonucleotides after amplification.

DETAILED DESCRIPTION OF THE INVENTION

Definitions

Artificial nucleotide: Nucleic acids not found in the nature e.g. but not limited to, iso-dCTP or iso-dGTP, with or without modifications, e.g., but not limited to, biotin and fluorophores and any of the natural nucleic acids containing modifications, e.g., but not limited to, biotin and fluorophores.

Biotin-coupled-oligonucleotide: An oligonucleotide with a bound biotin molecule e.g. to its 5'-end.

Closed circular structure: A nucleic acid sequence with a non-ending sugar-phosphate backbone.

Externally templated ligation: Ligation of the 5'-end and the 3'-end of the same or different oligonucleotides by hybridization to a template, which is not part of the oligonucleotide/oligonucleotides.

Hairpin: A section of single-stranded nucleic acid sequence that hybridises onto itself creating a single stranded nucleic acid loop and a double stranded nucleic acid region.

Ligation template: A nucleic acid sequence to which the 5'-end of one oligonucleotide and the 3'-end of the same or another oligonucleotide can hybridise and be aligned in a way, which allows ligation of the two ends.

LNA: Locked nucleic acids.

Mly I: A type IIS enzyme, which recognises the sequence 5'-GAGTCNNNNN-3' (SEQ ID NO:14) and cuts double stranded DNA blunt end after the last N creating a 3'-hydroxyl and a 5'-phosphate.

N: Any of the nucleotides G, C, A, T, I, U and any artificial nucleotides.

N.Alw I (Nt.Alw I): A nicking enzyme, which recognises the sequence 5'-GGATCNNNNN-3' (SEQ ID NO:15) and nicks the recognition sequence between the two last N's: 5'-GGATCNNNN-nicking-N (SEQ ID NO:16).

Natural nucleotide: Any of the nucleotides G, C, A, T, I, U.

Nicking cassette: A nucleic acid sequence comprising a loop and one or more complementary sequences, which enable parts of the nicking cassette to hybridise to parts of itself. The nicking cassette is able to bind one or more modifying enzymes, preferably nicking enzymes. If the nicking cassette is to be removed from the nucleic acid sequence to which it is added, it is designed as a suicide cassette.

Nicking enzyme: An enzyme, which recognises a double stranded nucleic acid sequence and is capable of cutting one and only one strand in the double stranded nucleic acid sequence, creating a 3'-hydroxyl and a 5'-phosphate.

Nucleic acid sequence: Any sequence containing natural nucleotides e.g., but not limited to, G, C, A, T, I, U or any artificial nucleotides e.g., but not limited to, iso-dCTP, iso-dGTP or a mixture thereof.

Nucleic acid probe (A): A nucleic acid sequence comprising the nucleic acid sequence of the one or more oligonucleotides to be amplified by the method of the invention and the nucleic acid sequence of one or more nicking cassettes.

Nucleic acid probe (B): A nucleic acid sequence complementary to nucleic acid sequence (A).

Nucleotide: Any natural, artificial or modified nucleotide.

Oligonucleotide: A single stranded nucleic acid sequence having a length of 10-1000 nucleotides, such as e.g. 10-800 nucleotides, or such as e.g. 10-600 nucleotides, or such as e.g. 10-500 nucleotides, or such as e.g. 15-400 nucleotides, or such as e.g. 15-300 nucleotides, or such as e.g. 20-250 nucleotides, or such as e.g. 20-200, or such as e.g. such as e.g. 20-180, or such as e.g. 20-160, or such as e.g. 25-140 nucleotides, or such as e.g. 30-130 nucleotides, or such as e.g. 40-120 nucleotides, or such as e.g. 50-110 nucleotides, or such as e.g. 60-110 nucleotides, or such as e.g.70-100 nucleotides.

PNA: Peptide nucleic acid.

Rolling circle replication: Nucleic acid synthesis using a circular single stranded oligonucleotide as rolling-circle-template and a short nucleic acid sequence as a primer. The addition of a DNA polymerase and dNTPs starts the polymerization. As the rolling-circle-template is endless the product will be a single long nucleic acid strand composed of tandem repeats complementary to the rolling-circle-template.

Rolling-circle-template: The closed circular nucleic acid sequence which a polymerase uses as template for rolling circle replication.

Self-templated ligation: Ligation of the 5'-end and the 3'-end of the same or different oligonucleotides by hybridization to a template which is part of the oligonucleotide, or part of one of the oligonucleotides.

Solid support: Any solid support an oligonucleotide can be attached to or synthesised on, e.g., but not limited to, PCR-tubes, microscopic slides, ELISA-plates, microchips, plastic CDs (produced by the company Amic), or beads.

Suicide cassette: A nucleic acid sequence comprising one or more complementary sequences, which enable parts of the suicide cassette to hybridise to parts of itself. The complementary sequences are separated by a loop. The suicide cassette is able to bind one or more modifying enzymes, preferably nicking enzymes and restriction enzymes. The suicide cassette can be removed from the nucleic acid sequence to which it is added by restriction digestion. A suicide cassette is a nicking cassette further comprising one or more restriction sites.

Type IIS enzyme: An enzyme which recognises asymmetric nucleotide sequences and cleaves DNA at a specified position outside of the recognition site.

Z: The one or more oligonucleotides to be amplified by the invention such as e.g. 1-10 oligonucleotides, or such as e.g. 1-5 oligonucleotides, or such as e.g. 3 oligonucleotides, or such as e.g. 2 oligonucleotides, or such as e.g. 1 oligonucleotide.

DESCRIPTION OF THE INVENTION

The present invention provides a method for the amplification of one or more oligonucleotides using a single-stranded probe as template for the amplification reaction. The probes of the invention for use in the method are composed of the one or more oligonucleotides to be amplified and one or more cassettes (nicking cassettes or suicide cassettes). The purpose, components and characteristics of the nicking cassette and the suicide cassette are outlined in detail below. The presence of the one or more nicking cassettes or one or more suicide cassettes in the probes of the invention makes it possible to amplify any oligonucleotide comprising a sequence of at least 10-1000 nucleotides by the method of the invention without any requirements on the nucleic acid sequence of the oligonucleotide, such as e.g. the presence of restriction sites.

The relationship between the nicking cassette and the suicide cassette is thus: i) all suicide cassettes are also nicking cassettes (and may be used as such), since they are nicking cassettes with an added feature, an element designed to enable their removal at convenience. ii) Since the nicking cassette is not removed, it equips the synthesis product with the functionalities of the nicking cassette, i.e. the possibility of self-templated ligation into a closed circular structure and reduction of polymers to monomers. The suicide feature does not equip the product with this functionality, but leaves it with freely designable 5'-ends and 3'-ends, such as e.g. needed in padlock probes. Nicking cassettes thus serve amplification purposes and add the feature of self-circularisation to the product, whereas the suicide element serves purification purposes only.

It is to be understood that an amplified product of probe (A), probe (B), the oligonucleotide contained within probe (A), and the oligonucleotide contained within probe (B) can be obtained by the use of this invention.

Thus, in one aspect of the invention, the invention relates to a method for amplifying an oligonucleotide contained within a nicking cassette through successive rounds of ligation, rolling circle replication, and nicking. The method comprises A method for amplifying one or more oligonucleotides comprising
  a) creating a nucleic acid probe (A) comprising one or more oligonucleotides and one or more nicking cassettes, and
  b) circularising of the probe (A), and
  c) providing a primer with a target sequence in part of said probe (A), and
  d) effecting rolling circle replication of said probe (A), and
  e) nicking of the rolling circle product of probe (A) within the one or more nicking cassettes obtaining multiple copies of a probe (B) complementary to the probe (A),
  f) circularising of the probe (B), and
  g) providing a primer with a target sequence in part of said probe (B), and
  h) effecting rolling circle replication of said probe (B), and
  i) nicking of the rolling circle product of probe (B) within the one or more nicking cassettes obtaining multiple copies of a probe (A) complementary to the probe (B).

To increase the amount of product, steps b-i can be repeated as many times as needed. If each round e.g. amplifies 300×, two rounds equals $300^2$× amplification, three rounds equals $300^3$× amplification and four rounds equals $300^4$× amplification. Thus, after four rounds 1 ng of probe (A) may be turned into about 8 grams of probe (A), enough for several million individual application reactions. Obviously, the larger production of oligonucleotides occurs in the later cycles, so for large scale production the reaction is cycled more than once.

In one embodiment, the method according to the invention relates to a method, wherein steps b)-i) are performed one or more times, such as e.g. 1-100 times, or such as e.g. 1-50 times, or such as e.g. 1-25 times, or such as e.g. 1-10 times, or such as e.g. 1-5 times, or such as e.g. 1-4 times, or such as e.g. 1-3 times, or such as e.g. 1-2 times. In another embodiment, the method according to the invention relates to a method, wherein steps b)-i) are performed one or more times, such as e.g. one time, or such as e.g. two times, or such as e.g. three times, or such as e.g. four times, or such as e.g. five times, or such as e.g. six times, or such as e.g. seven times, or such as e.g. eight times, or such as e.g. nine times, or such as e.g. ten times.

In a second embodiment, the method according to the invention relates to a method wherein probe (A) is acquired after step i).

In a third embodiment, the method according to the invention relates to a method wherein probe (B) is acquired after step e)

The nucleic acid probe of the invention comprises the one or more oligonucleotides to be amplified by the method of the invention and one or more nicking cassettes, wherein the nicking cassette is a nucleic acid sequence comprising one or more complementary sequences, enabling parts of the nicking cassette to hybridise to parts of itself. This makes it possible for the probe of the invention to circularise by self-templated ligation. The nicking cassette is furthermore able to bind one or more modifying enzymes, preferably a nicking enzyme. This allows the nicking cassette and the oligonucleotide contained within it to be amplified through successive rounds of ligation, rolling circle replication, and nicking. Thus, in one embodiment, the invention relates to a nucleic acid probe comprising one or more oligonucleotides and one or more nicking cassettes, wherein the one or more nicking cassettes are nucleic acid sequences comprising one or more complementary sequences and one or more nicking sites.

The purpose and characteristics of the nicking cassette are outlined below in details.
The Nicking Cassette The nicking cassette of the invention is a nucleic acid sequence. The nicking cassette can comprise any sequence of the natural nucleotides G, C, A, T, I, U, or any artificial nucleotides e.g., but not limited to, iso-dCTP, iso-dGTP, or a mixture thereof. The nicking cassette of the invention has a linear length of 20-200 nucleotides. Thus, in one aspect, the invention relates to a method, wherein the one or more nicking cassettes have a length of 20-200 nucleotides, such as e.g. 20-150 nucleotides, or such as e.g. 20-100 nucleotides, or such as e.g. 20-80 nucleotides, or such as e.g. 20-60 nucleotides, or such as e.g. 20-40 nucleotides, or such as e.g. 20-30 nucleotides.

The aim of the nicking cassette is to enable amplification of an oligonucleotide by applying the method of the invention, which is based on the principle of rolling circle replication. The nicking cassette is added to the sequence of the oligonucleotide to be amplified before the initiation of the rolling circle replication, most conveniently during the initial synthesis of probe (A). Thus, the nicking cassette is attached to the sequence of the oligonucleotide to be amplified during the steps of the rolling circle replication.

Figure 2:
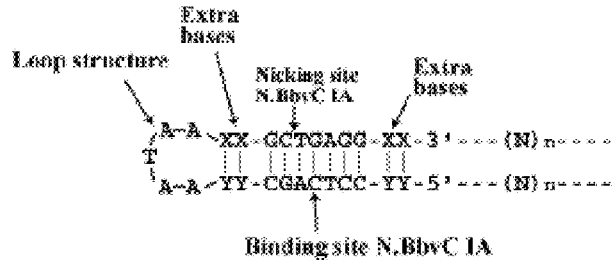
Figure 2:
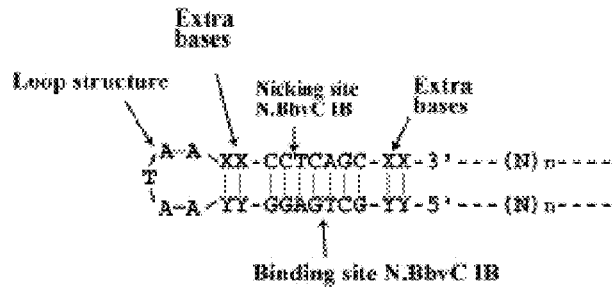
Figure 2:
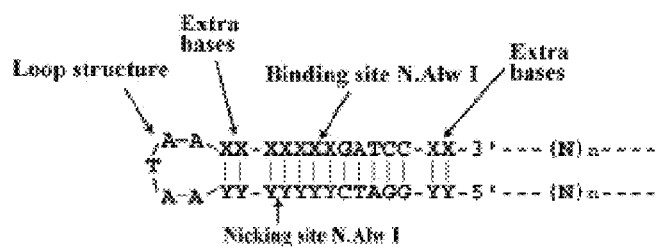
Figure 2:
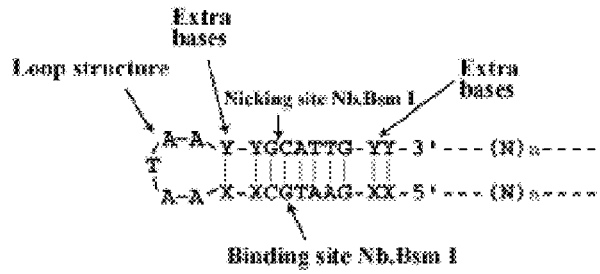

The nicking cassette possesses several characteristics: 1) the cassette comprises one or more complementary sequences, enabling the cassette to hybridise to itself, 2) the cassette comprises one or more sites for nicking enzymes, and 3) the cassette comprises a loop structure (FIG. 2).

The different characteristics of the nicking cassette are described below:
Loop Structure of the Nicking Cassette The loop structure of the nicking cassette aims to connect the ends of the two complementary sequences. The loop comprises 3-100 nucleotides, such as e.g. 3-80 nucleotides, or such as e.g. 3-60 nucleotides, or such as e.g. 3-40 nucleotides, or such as e.g. 3-20 nucleotides, or such as e.g. 3-10 nucleotides, or such as e.g. 3-9 nucleotides, or such as e.g. 3-8, or such as e.g. 3-7 nucleotides, or such as e.g. 3-6 nucleotides, or such as e.g. 3-5 nucleotides. Preferably, the loop sequence is 3-7 nucleotides long (FIG. 2), such as e.g. 3 nucleotides, or such as e.g. 4 nucleotides, or such as e.g. 5 nucleotides, or such as e.g. 6 nucleotides, or such as e.g. 7 nucleotides. Examples of loop structures include, but not limited to: 5'-AATAA-3' for the (+)-strand and 5'-TTATT-3' for the (−)-strand, 5'-GM-3' for the (+)-strand and 5'-TTC-3' for the (−)-strand, 5'-GAAA-3' for the (+)-strand and 5'-TTTC-3' for the (−)-strand, or 5'-AAAA-3' for the (+)-strand and 5'-TTTT-3' for the (−)-strand. The (+)-strand is the loop-sequence of probe (A), while the (−)-strand is the loop-sequence of probe (B). The loop structure can be selected from but is not limited to the group consisting of AATAA, GAA, GAA, AAAA, and TTTT for the (+)-strand. Thus, in one embodiment, the invention relates to a method, wherein the one or more nicking cassettes comprise a loop-structure selected from the group consisting of AATAA, GAA, GAA, AAAA, and TTTT. This means that the sequence of the nicking cassette in probe (A) is selected from but not limited to the group consisting of AATAA, GAA, GAA, AAAA, and TTTT. If a strong hairpin in the loop structure is needed, it is recommendable to have 5'-GAM-3' or 5'-GM-3' in the loop, as these two sequences are known to increase the melting temperature for a hairpin considerably (Hirao I et al. Nucleic Acids Res. 17(6), 2223-31 (1989) and Hirao I et. al Nucleic Acids Res. 22(4), 576-82 (1994)).
Complementary Sequences of the Nicking Cassette The complementary sequences of the nicking cassette are positioned on each side of the loop structure in the sequence of the nicking cassette (FIG. 2). The complementary sequences comprise 10-100 nucleotides, such as e.g. 10-80 nucleotides, such as e.g. 10-60 nucleotides, such as e.g. 10-30 nucleotides, or such as e.g. 10-40 nucleotides. Preferably, the complementary sequences are 10-20 nucleotides long, such as e.g. 10-20 nucleotides, such as e.g. 12-20 nucleotides, such as e.g. 14-20 nucleotides, or such as e.g. 15-20 nucleotides. Examples of complementary sequences are, but not limited to:

```
5'-XXGCTGAGGXX-3'
and

5'-YYCCTCAGCYY-3'
and

5'-XXCCTCAGCXX-3'
and

5'-YYGCTGAGGYY-3',
and

5'-XXXXXXXGATCCXX-3'
and

5'-YYGGATCYYYYYYY-3',
and

5'-XXGAATGCXX-3'
and

5'-YYGCATTCYY-3'
``` wherein X and Y are any pair of natural or artificial nucleotides which can hybridize to each other.

In one embodiment, the invention relates to a method, wherein the one or more nicking cassettes comprise the complementary sequences:

```
5'-XXGCTGAGGXX-3'
and

5'-YYCCTCAGCYY-3',
and
``` wherein X and Y are any pair of natural or artificial nucleotides which can hybridize to each other.

In a second embodiment, the invention relates to a method, wherein the one or more nicking cassettes comprise the complementary sequences:

```
5'-XXCCTCAGCXX-3'
and

5'-YYGCTGAGGYY-3',
and
``` wherein X and Y are any pair of natural or artificial nucleotides which can hybridize to each other.

In a third embodiment, the invention relates to a method, wherein the one or more nicking cassettes comprise the complementary sequences:

```
5'-XXXXXXXGATCCXX-3'
and

5'-YYGGATCYYYYYYY-3',
and
``` wherein X and Y are any pair of natural or artificial nucleotides which can hybridize to each other.

In a fourth embodiment, the invention relates to a method, wherein the one or more nicking cassettes comprise the complementary sequences:

```
5'-XXGAATGCXX-3'
and

5'-YYGCATTCYY-3'
``` wherein X and Y are any pair of natural or artificial nucleotides which can hybridize to each other.

The aim of the complementary sequences of the nicking cassette is to form binding sites for nicking enzymes. Furthermore, the complementary sequences enable the probe (A) or (B) to be circularized by self-templated hybridization of the complementary sequences in the nicking cassette.

Preferably, parts of the nicking cassette will be added to each end of the oligonucleotide sequence to be amplified during the initial synthesis. Preferably, a minimum of 5 nucleotides able to accommodate self-templated hybridization is positioned at each end of the oligonucleotide. Alternatively, the nicking cassette is positioned central in the probe (A). In this case circularisation can be performed by externally templated ligation of one or more oligonucleotides.

Binding Site for the Nicking Enzyme in the Nicking Cassette

The nicking cassette comprises a recognition site for one or more nicking enzymes. As outlined in the definitions, a nicking enzyme recognises a double stranded nucleic acid sequence and cuts one and only one strand in the double stranded nucleic acid sequence, creating a 3'-hydroxyl and a 5'-phosphate. The nicking enzyme is used in step e) and step i) of the method of the invention. In step e) the rolling circle product of the first amplification round, comprising multiple copies of the complementary sequence to probe (A) (probe (B)), is exposed to the nicking enzyme. The amplified product comprises a multimer of successive copies of probe (B). Each nicking cassette sequence is forming a hairpin as the complementary sequences in the nicking cassette are hybridising to each other. The nicking enzyme recognises the nicking site in the double stranded hairpin region of the nicking cassette and cuts one strand in the double stranded sequence. Thus, the cutting of the amplified product by the nicking enzyme results in multiple copies of probe (B). Thereby, the nicking enzyme prepares the rolling circle product of the first amplification round for the second round of ligation, rolling circle replication, and nicking. Furthermore, the nicking enzyme is used in step i) of the method of the invention. In step i) the rolling circle product of the second amplification round, comprising multiple copies of the complementary sequence to the probe (B) (probe (A)), is exposed to the nicking enzyme. The cutting of the amplified product of the second amplification round by the nicking enzyme results in multiple copies of probe (A). Thereby, the nicking enzyme prepares the rolling circle product of the second amplification round for additional rounds of rolling circle replication (step b) to step i) of the method of the invention).

Additional base pairs on either side of the binding site for the nicking enzyme in the complementary sequences of the nicking cassette may be included to increase the cleavage efficiency of the nicking enzyme (FIG. 2). Preferably, two base pairs are inserted on either side, alternatively 0-50 base pairs are inserted on one or both sides, such as e.g. 0-40 base pairs on one or both sides, or such as e.g. 0-30 base pairs on one or both sides, or such as e.g. 0-20 base pairs on one or both sides, or such as e.g. 0-10 base pairs on one or both sides, or such as e.g. 0-8 base pairs on one or both sides, or such as e.g. 0-6 base pairs on one or both sides, or such as e.g. 0-4 base pairs on one or both sides.

In general the extra base pairs can be freely chosen as long as they are not identical to the enzyme binding sites already used, or create additional binding sites for the enzymes to be used.

At the moment, a limited number of nicking enzymes are available on the market, and therefore only a few nicking cassettes can be designed. In the future, nicking enzymes with higher cleavage efficiencies and more narrow recognition sites will most likely be developed. This will allow new designs of nicking cassettes, possibly limiting the size of the nicking cassette and/or increasing the amplification efficiency.

The detailed structure of the nicking cassette may vary, as the position of the binding site for the nicking enzyme, the number of extra nucleotides, and the nucleotide composition of the loop all can be adjusted for optimal performance in the amplification reaction. The sequence of the binding site for the nicking enzyme also depends on the specific enzyme used.

As an alternative to using the nicking cassette for self-templated ligation, the circularisation of probe (A) in the step b) can be obtained by externally templated ligation of one or more oligonucleotides.

Examples of nucleic acid sequences of the nicking cassette include, but are not limited to:

5'-YYCCTCAGCYYAATAAXXGCTGAGGXX-3' (FIG. 2A),

5'-YYGCTGAGGYYAATAAXXCCTCAGCXX-3' (FIG. 2B),

5'-YYGGATCYYYYYYYAATAAXXXXXXXGATCCXX-3' (FIG. 2C), and

5'-YYGAATGCYYAATAAXXGCATTCXX-3' (FIG. 2D)

wherein X and Y are any pair of natural or artificial nucleotides which can hybridize to each other.

In one aspect, the invention relates to a method, wherein the one or more nicking cassettes comprise a nucleic acid sequence selected from the group consisting of

5'-YYCCTCAGCYYAATAAXXGCTGAGGXX-3',

5'-YYGCTGAGGYYAATAAXXCCTCAGCXX-3',

5'-YYGGATCYYYYYYYAATAAXXXXXXXGATCCXX-3', and

5'-YYGAATGCYYAATAAXXGCATTCXX-3' wherein X and Y are any pair of natural or artificial nucleotides which can hybridize to each other.

In the following the different steps in the method of the invention are described in detail:

The one or more oligonucleotides to be amplified by the method of the invention can comprise a sequence of at least 10-1000 nucleotides. Thus in one aspect, the invention relates to a method, wherein the one or more oligonucleotides comprise a sequence of 10-1000 nucleotides, such as e.g. 10-800 nucleotides, or such as e.g. 10-600 nucleotides, or such as e.g. 10-500 nucleotides, or such as e.g. 15-400 nucleotides, or such as e.g. 15-300 nucleotides, or such as e.g. 20-250 nucleotides, or such as e.g. 20-200, or such as e.g. such as e.g. 20-180, or such as e.g. 20-160, or such as e.g. 25-140 nucleotides, or such as e.g. 30-130 nucleotides, or such as e.g. 40-120 nucleotides, or such as e.g. 50-110 nucleotides, or such as e.g. 60-110 nucleotides, or e.g. such as 70-100 nucleotides.

In a preferred embodiment, the invention relates to method wherein the one or more oligonucleotides are DNA oligonucleotides.

The oligonucleotide can comprise any nucleic acid sequence composed of any of the natural deoxyribonucleotides G, C, A, T, and any of the artificial nucleotides, iso-dCTP, iso-dGTP, or any natural or artificial nucleotides containing modifications. Preferably, the invention relates to a method, wherein the one or more oligonucleotides are DNA sequences.

In the case where artificial base pairs, such as iso-dCTP, iso-dGTP, or both, are included in the oligonucleotide to be amplified, or in the nicking cassette, the genetic alphabet is expanded to contain three base pairing components; G-C, A-T, and e.g. isoG-isoC.

Creation of Probe (A) (Step a)

The starting nucleic acid sequence (probe (A)), which comprises one or more oligonucleotides to be amplified and one or more nicking cassettes, can be synthesised by standard chemical methods, such as e.g. beta-cyanoethyl phosphoramidite chemistry. The 5'-phosphate can be added during this synthesis, or alternatively the 5'-phosphate can be coupled enzymatically to the 5'-end of the nucleic acid sequence, by e.g. using T4 polynucleotide kinase.

Figure 5:
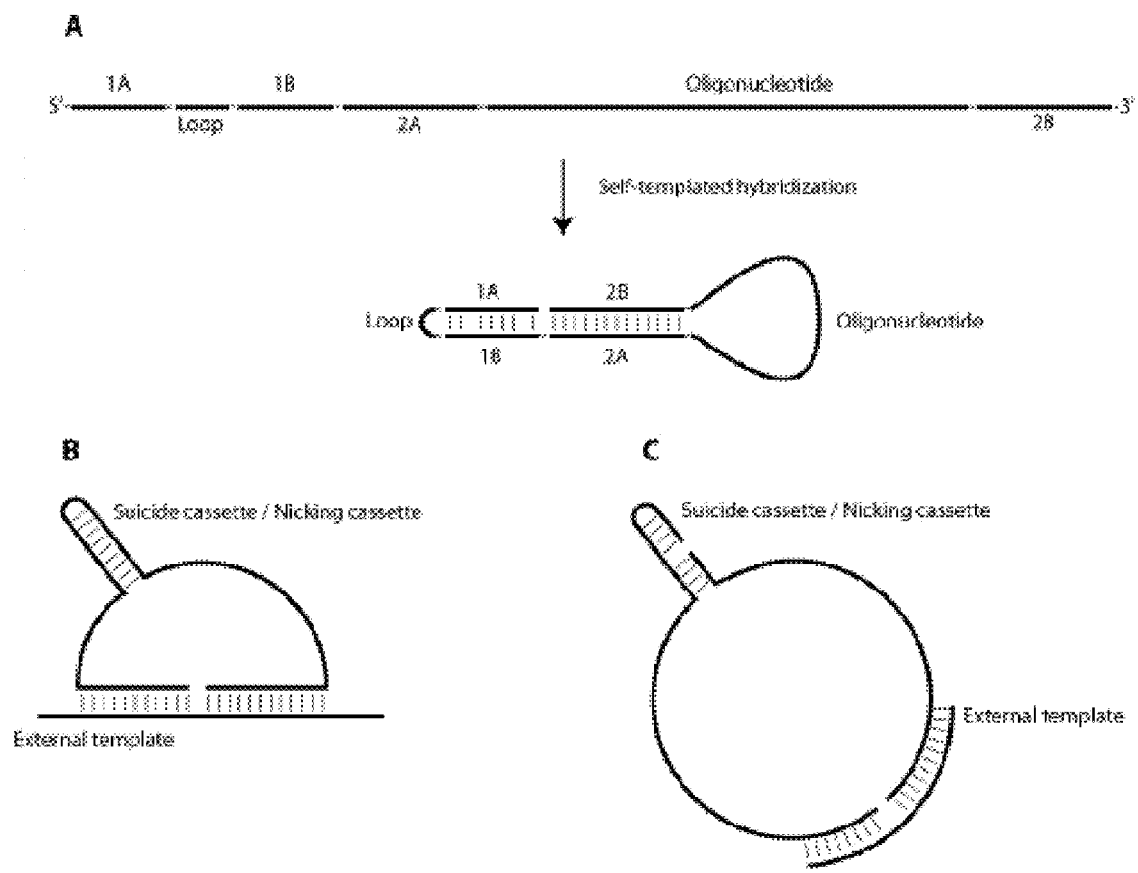

Long sequences can be constructed by externally templated ligation of multiple oligonucleotides, e.g. when the oligonucleotide to be amplified is very long e.g. 200-1000 nucleotides. In this situation, probe (A) can be created by externally templated ligation of two or more oligonucleotides (FIG. 5). In one embodiment, the invention relates to a method, wherein the probe (A) is created by ligation of one or more nucleic acid sequences comprising one or more parts of the one or more oligonucleotides and the one or more nicking cassettes.

Preferably, the probe (A) will contain a part of the nicking cassette in each end of the probe. Alternatively the nicking cassette is positioned centrally in the oligonucleotide. If the probe (A) is created by externally templated ligation of several synthesized sequences, a part of the nicking cassette can be positioned at the 3'-end of one sequence and another part can be positioned in the neighboring 5'-end of another sequence. Alternatively the cassette can be positioned centrally in one or more of the synthesized sequences. The start nucleic acid sequence (probe (A)) can also contain more than one nicking cassette, which can be either identical or different in design, i.e. nucleic acid composition.

In one aspect, the invention relates to a method, wherein the probe (A) comprises a nucleic acid sequence selected from the group consisting of:

5'-P-GAGGXX-Z-YYCCTCAGCYYAATAAXXGCT-3',

5'-P-CAGCXX-Z-YYGCTGAGGYYAATAAXXCCT-3',

5'-P-XXGATCCXX-Z-YYGGATCYYYYYYYAATAAXXXXX-3', and

5'-P-TTCYY-Z-XXGAATGCYYAATAAXXGCA-3' wherein

Z is the one or more oligonucleotides to be amplified,

X and Y are any pair of natural or artificial nucleotides which can hybridize to each other, P is a 5'-phosphate.

Circularisation of Probe (A) (Step b)

Circularisation of probe (A) can be performed by self-templated ligation or by externally templated ligation or a combination of both. In case probe (A) contains a part of the nicking cassette in each end of probe (A), ligation can be performed by self-templated ligation (FIG. 5A). As seen in FIG. 5A, by hybridization between element 1A-1B and element 2A-2B, the nucleic acid probe folds into an open circle by self-templated hybridization. If the nicking cassette is positioned centrally in an oligonucleotide, ligation can be performed by externally templated ligation of one or more oligonucleotide (FIG. 5B). For long oligonucleotides, probe (A) can e.g. be constructed by ligation of more than one nucleic acid sequence, e.g. by a combination of self-templated hybridisation and externally templated hybridisation (FIG. 5C). Thus, in one embodiment, the invention relates to a method, wherein the closed circular structure of nucleic acid probe (A) is obtained by self-templated ligation. As outlined above, the circularisation of probe (A) can be obtained by self-templated hybridization of the probe (A) via hybridisation of the complementary regions of the one or more nicking cassettes within the probe (A), to enable ligation of the ends of probe (A).

A closed circular structure can be created by standard enzymatic ligation for both externally templated ligation and self-templated ligation, by applying the correct buffer conditions together with the appropriate energy source (ATP or NAD+) and a ligase. Preferably the T4 DNA ligase is used. ATP is supplied in a concentration of 0.001-10 mM preferably 0.1-1 mM, T4 DNA ligase is supplied in a final concentration of 0.00025-0.1 Weiss unit/µl, preferably 0.0025-0.05 U/µl. Alternatively, other ligases such as Tsc ligase, Tth ligase, Ampligase, and Taq ligase, can be used. Chemical ligation may also be used. A circle containing one or more nicking cassettes will typically comprise 50-1000 nucleotides, preferably 50-500 nucleotides.

Primer Structure

For a standard DNA polymerase, a primer is needed to start the rolling circle replication reaction. In general, a primer consists of 5-50 nucleotides and preferably of 7-15 nucleotides. The primer has to be complementary to part of the nucleic acid probe, preferably a part outside the nicking cassette, alternatively a part inside the nicking cassette.

Preferably the primer is 100% complementary to the probe, alternatively nucleotides at the 5'-end of the primer are non-complementary to the probe, e.g. 1 nucleotide, 3 nucleotides, 5 nucleotides, 10 nucleotides, 25 nucleotides or 50 nucleotides. If a polymerase containing 3' to 5' exonuclease activity is used (e.g. Phi29 DNA polymerase), non-complementary nucleotides at the 3'-end of the primer can be present, such as e.g. 1 nucleotide, such as e.g. 3 nucleotides, such as e.g. 5 nucleotides, such as e.g. 10 nucleotides, such as e.g. 25 nucleotides, or such as e.g. 50 nucleotides. Furthermore, mismatched nucleotides in the primer can be present, e.g. 1 nucleotide, such as e.g. 3 nucleotides, such as e.g. 5 nucleotides, such as e.g. 10 nucleotides, or such as e.g. 25 nucleotides.

The primer can be synthesised by standard chemical methods (e.g. beta-cyanoethyl phosphoramidite chemistry). A primer can also contain modifications e.g., but not limited to, streptavidine, avidin, biotin, $^{32}P$, and fluorophores, or it may comprise artificial nucleotides such as, but not limited to, LNA, PNA, iso-dCTP, and iso-dGTP.

For correct annealing between circle and primer, a molar ratio of 0.1-100 between circle and primer is mixed, preferably 0.8-1.2.

It is to be understood that polymerases which do not need a primer can also be used by the method of the invention, In this case no primers are needed to start the rolling circle replication.

For production purposes, an improvement of the procedure can be obtained by letting one or more reagents, e.g. the primers, in step c and/or step g of the method of the invention, be anchored to a solid support, thereby attaching the rolling circle product to a surface. This will make it easier to change buffer conditions, and improve washing between the different steps, thereby minimizing background. In one example, the primer can be coupled in the 5'-end to a solid support—a 5'-biotin labelled primer may e.g. be coupled to a streptavidine coated solid support including, but not limited to, PCR-tubes, ELISA plates, beads, plastic CDs (produced by the company Amic), and microscope slides. Introduction of coupling of the primer to a solid support allows stringent washing after each round of rolling circle replication to remove the rolling-circle-template, thereby leaving only the coupled rolling circle product. This will minimize the production of the "wrong" strand in the second round of rolling circle replication. Microfluidics solutions provide a set of platforms where reagents can be anchored and conditions can be changed all within one design. Besides the physical anchoring of reagents (e.g. primer, polymerase) microfluidics systems also provide means of confining reagents to defined compartments, permanently or transiently, without attaching them to a support, i.e. a non-physical anchoring. Either the primer, the nucleic acid circle, the polymerase, or the endonucleases may thus be attached to a solid support or otherwise confined spatially without seriously damaging the overall efficiency of the amplification reaction. In the case of the circle, the circle can be locked around a structure on the support allowing rolling of the circle but inhibiting the circle from diffusing away from the surface.

Thus, in one aspect, the invention relates to a method, wherein the primer in step c is immobilised on a solid support.

In another aspect, the invention relates to a method, wherein the primer in step g is immobilised on a solid support.

In a third aspect, the invention relates to a method, wherein nucleic acid circle is attached to a solid support or otherwise spatially confined.

In a fourth aspect, the invention relates to a method, wherein the polymerase is attached to a solid support or otherwise spatially confined.

In a fifth aspect, the invention relates to a method, wherein the endonucleases are immobilised on a solid support or otherwise spatially confined.

First Rolling Circle Replication

When a polymerase and deoxynucleotide triphosphates (dNTPs) are combined with a probe hybridized to a primer (primer 1) under correct buffer conditions, rolling circle replication can take place. The polymerase will start the polymerization from the 3'-end of the primer, using the circular probe as a rolling-circle-template. As the circular probe is endless, the rolling circle product will comprise a multimer complementary to the sequence of the circular probe. Preferably the polymerase is the Phi29 DNA polymerase. A final concentration of 0.001-2 units of phi29 polymerase (Fermentas) is used, preferably 0.05-1 unit is used. A final dNTP concentration of 0.005-10 mM, preferably 0.1-1 mM is used. Alternatively, other polymerases such as the T7 DNA polymerase, Sequenase Version 2.0 T7 DNA Polymerase, and Bst DNA polymerase can be used. The incubation time should be between 10 minutes and 24 hours, preferably 30 minutes to 5 hours, at the temperature optimal for the polymerase of choice. For some of the polymerases addition of single stranded binding protein (SSB) strongly enhances the rolling circle activity. Since the Phi29 DNA polymerase is not enhanced by SSB, a concentration of 0 µg/µl SSB is preferably used. Alternatively a concentration of 0.001-0.2 µg/µl can be used.

The length of the rolling circle product is preferably between 500 and 500,000 nucleotides in length. The speed and duration of the elongation can be controlled by varying the concentrations of dNTP, polymerase, circle, primer, and SSB. Furthermore, temperature and buffer conditions are adjustable.

Nicking of Rolling Circle Product

The rolling circle product, which comprises multiple copies of a complementary sequence to probe (A) (called probe (B)), will fold into distinct hairpins, each composed of a nicking cassette. To turn the multimer into monomers without the loss of nucleotides, the multimer is cut with a nicking enzyme. The binding site of the nicking enzyme is positioned in the nicking cassette. The preferred nicking enzymes are N.Alw I (Nt.Alw I), N.BbvC IA (Nb.BbvC I), N.BbvC IB (Nt.BbvC I), Nt.BstNB I, Nb.Bpu10I and Nb.Bsm I. Thus, in one embodiment, the invention relates to a method, wherein the nicking enzyme is selected from the group consisting of N.Alw I (Nt.Alw I), N.BbvC IA (Nb.BbvC I), N.BbvC IB (Nt.BbvC I), and Nb.Bsm I. Preferably, the N.Alw I (Nt.Alw I) is in the method of the invention. Therefore, in a preferred embodiment, the invention relates to a method, wherein the nicking enzyme is N.Alw I (Nt.Alw I). Preferably the buffer mixture is adjusted to accommodate nicking conditions without a purification step, alternatively the rolling circle product is purified by known methods (e.g. gel purification or ethanol precipitation) and optimal buffer conditions for the nicking enzyme is supplied. Preferably 0.3-1 U/μl of nicking enzyme is used alternatively 0.05-3 U/μl is used. Incubation time can be from 30 minutes to 3 days, preferably 3-20 hours.

Purification of the Nicked Rolling Circle Product

The nicked product can be acquired following a nicking reaction by standard purification methods e.g. by gel purification, ethanol precipitation or HPLC purification.

Second Ligation

To turn the nicked product into a closed circular structure, a denaturation-renaturation step by heating and cooling may be performed, which will promote the monomers (multiple copies of probe (B)) to fold into an open circular structure by self-templated hybridization in the region of the nicking cassette (FIG. 1). Thus, circularisation of probe (B) can be obtained by intra-molecular hybridization of the probe (B) via hybridisation of the complementary regions of the one or more nicking cassettes, enabling ligation of the ends of probe (B). Therefore, one embodiment of the invention relates to a method, wherein the circularisation of probe (B) is obtained by self-templated ligation.

A closed circular structure of probe (B) can be created by standard enzymatic ligation. Preferably, the buffer conditions are adjusted to improve ligation without a purification step, alternatively the nicked product is purified by known methods (e.g. gel purification or ethanol precipitation), before ligation.

Second Rolling Circle Replication

The second rolling circle replication is performed similarly to the first rolling circle replication. Preferably, the primer (primer 2) is complementary to the one used in the first round of rolling circle replication, alternatively it hybridizes to another part of the probe sequence than primer 1.

Nicking of the Rolling Circle Product of the Second Round

This step of the reaction is similar to the nicking of the rolling circle product of the first round. The difference from the first round of nicking is that it is now a tandem repeat of probe (A) which is nicked and not a tandem repeat of probe (B).

Following nicking with the nicking enzyme, the product can be purified e.g. by gel purification, ethanol precipitation or HPLC purification. Alternatively the nicking product is amplified further by successive rounds of ligation, rolling circle replication, and nicking as outlined above.

Thus, in one embodiment, the invention relates to a method wherein probe (A) is amplified through successive rounds of ligation, rolling circle replication, and nicking.

In another embodiment, the invention relates to a method wherein probe (B) is amplified through successive rounds of ligation, rolling circle replication, and nicking as outlined above.

The Probe of the Invention

The invention also relates to a nucleic acid probe comprising one or more nicking cassettes, wherein said one or more nicking cassettes are nucleic acid sequences comprising one or more complementary sequences, and one or more nicking sites. The details of the complementary sequences and nicking sites are as outlined above.

Furthermore, the probe of the invention comprises one or more oligonucleotides for amplification by the method of the invention. Thus, the invention relates to a nucleic acid probe comprising one or more oligonucleotides and one or more nicking cassettes, wherein the one or more nicking cassettes are nucleic acid sequences comprising one or more complementary sequences and one or more nicking sites. As outlined above, the one or more oligonucleotides for amplification by the method of the invention comprise a sequence of at least 10-1000 nucleotides. Therefore in one aspect, the invention relates to a nucleic acid probe, wherein the one or more oligonucleotides comprise a sequence of 10-1000 nucleotides.

As mentioned, the details of the complementary sequences and the nicking sites for the nicking cassette comprised in the probe of the invention are as outlined under the method of the invention.

Therefore, in one embodiment, the invention relates to a nucleic acid probe, wherein the one or more nicking cassettes have a length of 20-200 nucleotides.

In a second embodiment, the invention relates to a nucleic acid probe, wherein the one or more nicking cassettes comprise a loop-structure selected from the group consisting of AATAA, GAA, GAA, AAAA, and TTTT.

In a third aspect, the invention relates to a nucleic acid probe, wherein the one or more nicking cassettes comprise the complementary sequences:

```
5'-XXGCTGAGGXX-3'
and

5'-YYCCTCAGCYY-3',
and
``` wherein X and Y are any pair of natural or artificial nucleotides which can hybridize to each other.

In another embodiment, the invention relates to a nucleic acid probe, wherein the one or more nicking cassettes comprise the complementary sequences:

```
5'-XXCCTCAGCXX-3'
and

5'-YYGCTGAGGYY-3',
and
``` wherein X and Y are any pair of natural or artificial nucleotides which can hybridize to each other.

In yet another embodiment, the invention relates to a nucleic acid probe, wherein the one or more nicking cassettes comprise the complementary sequences:

```
5'-XXXXXXXGATCCXX-3'
```
and
```
5'-YYGGATCYYYYYY-3',
```
and wherein X and Y are any pair of natural or artificial nucleotides which can hybridize to each other.

In a further embodiment, the invention relates to a nucleic acid probe, wherein the one or more nicking cassettes comprise the complementary sequences:

```
5'-XXGAATGCYXX-3'
```
and
```
5'-YYGCATTCYY-3'
``` wherein X and Y are any pair of natural or artificial nucleotides which can hybridize to each other.

In yet another embodiment, the invention relates to a nucleic acid probe, wherein the one or more nicking cassettes comprise a nucleic acid sequence selected from the group consisting of:

```
5'-YYCCTCAGCYYAATAAXXGCTGAGGXX-3',

5'-YYGCTGAGGYYAATAAXXCCTCAGCXX-3',

5'-YYGGATCYYYYYYYAATAAXXXXXXXGATCCXX-3',
```
and
```
5'-YYGAATGCYYAATAAXXGCATTCXX-3'
``` wherein X and Y are any pair of natural or artificial nucleotides which can hybridize to each other.

In another aspect, the invention relates to a nucleic acid probe, wherein the probe comprises a nucleic acid sequence selected from the group consisting of:

```
5'-P-GAGGXX-Z-YYCCTCAGCYYAATAAXXGCT-3',

5'-P-CAGCXX-Z-YYGCTGAGGYYAATAAXXCCT-3',

5'-P-XXGATCCXX-Z-YYGGATCYYYYYYYAATAAXXXXX-3',
```
and
```
5'-P-TTCXX-Z-YYGAATGCYYAATAAXXGCA-3'
``` wherein

Z is the one or more oligonucleotides to be amplified,

X and Y are any pair of natural or artificial nucleotides which can hybridize to each other, P is a 5'-phosphate.

For production purposes, it may be desirable not to acquire the entire nicked product, but leave a batch for further rounds of amplification.

The nucleic acid probe of the invention can be used in rolling circle replication for different purposes—For example as a probe for use in the detection of nucleic acid molecules in situ (an in vitro diagnostic method).

The probes in this context can be used for the detection of single nucleic acid molecules by rolling circle replication. The probes mentioned below can be used for in vitro diagnostics and in diagnostic kits.

Using a probe which can be turned into a closed circular structure by self-templated ligation may be preferable when the ligation efficiency on the target nucleic acid molecule is low (e.g. on RNA targets or on DNA targets containing modifications resulting from degradation, preparation, or fixation, such as e.g. addition of mono-methylol (—$CH_2OH$) groups to the bases of the nucleic acids, resulting in dimerisation of adenine groups by methylene bridging). Procedures to revert such base-modification have been published (Masuda N. et al. Nucleic Acids Res. 15; 27(22) 4436-43 (1999)), but they only reduce the damage, since complete removal of all modifications is not possible. Another advantage of the probe is that the self-contained ligation template is a stretch of naked DNA which, compared to externally templated ligation using e.g. chromatin DNA, should result in higher ligation efficiency. Thus, in one embodiment, the invention relates to a nucleic acid probe further comprising a part comprising a sequence of nucleic acid residues, which is at least 75% complementary to a target nucleic acid sequence, such as e.g. 75-100% complementary, or such as e.g. 80-100% complementary, or such as e.g. 85-100% complementary, 90-100% complementary, or such as e.g. 95-100% complementary, or such as e.g. 100% complementary. This part could for instance be part of the oligonucleotide contained within the nicking cassette.

Target primed rolling circle reactions are primed from the natural 3'-end of a target nucleic acid molecule. Detecting nucleic acid molecules by target primed rolling circle replication has the advantage of strong signal amplification and a localised signal due to the target primed reaction (WO 97/20948 and Larsson C. et al. Nature Methods 1, 227-32 (2004)). Since this requires the presence of a 3'-end at or near the region in the RNA where the probe hybridises, the target RNA can preferably be a non-polyadenylated RNA, such as, but not limited to, EBER1 and EBER2 from the Epstein-Barr virus, the adenovirus-encoded small RNA's VA1 and VA2, ribosomal RNA's, the RNA part of the telomerase complex (hTERC), small interfering RNA's (siRNA's), and micro-RNA's (miRNA's).

On RNA targets, a preferred embodiment of the invention relates to a circular nucleic acid probe comprising a part of nucleic acid residues, wherein a part comprises a sequence of nucleic acid residues, which is at least 75% complementary to a target RNA sequence, such as e.g. 75-100% complementary, or such as e.g. 80-100% complementary, or such as e.g. 85-100% complementary, 90-100% complementary, or such as e.g. 95-100% complementary, or such as e.g. 100% complementary. This part could for instance be part of the oligonucleotide contained within the nicking cassette.

The part of the probe, comprising a nucleic acid sequence complementary to a target nucleic acid sequence, can have a linear length of 6-100. Thus, in one embodiment, the invention refers to a circular nucleic acid probe, wherein the length of a part is 6-100 nucleotides, such as e.g. 20-100 nucleotides, or such as e.g. 20-80 nucleotides, or such as e.g. 20-60 nucleotides, or such as e.g. 20-40 nucleotides, or such as e.g. 20-30 nucleotides.

In order to identify a probe, or distinguish between different probes, if more than one probe is present in a reaction, an element defining the particular probe, an identifier, is required. Thus, in one embodiment, the invention relates to a circular nucleic acid probe, further comprising one or more elements defining the specific probe.

Different methods can be used to identify a specific probe, and the identifier element will differ depending upon the choice of method.

If detection is obtained through hybridisation of labelled oligonucleotides to identifier elements, the identifiers need to have a certain length to be specific to a target sequence and to allow hybridisation under the reaction conditions. In theory, an identifier could match the total length of the probe, but in most cases a shorter identifier element would be preferable. Shorter identifiers would have faster hybridisation kinetics and would enable a probe to contain more than one identifier. Thus, in one embodiment, the invention relates to an element defining the specific probe, which is a nucleotide sequence of 6-200 nucleotides, such as e.g. 6-150 nucleotides, or such as e.g. 6-150 nucleotides, or such as e.g. 6-100 nucleotides, or such as e.g. 6-80 nucleotides, or such as e.g. 6-60 nucleotides, or such as e.g. 6-50 nucleotides, or such as e.g. 10-40 nucleotides, or such as e.g. 10-30 nucleotides, or such as e.g. 15-30 nucleotides.

However, since the probes are used as rolling-circle-templates in a rolling circle replication reaction, detection can also be obtained through synthesis. Such detection through synthesis could be performed similar to established linear PRINS reactions. Whereas incorporation of a labelled (e.g. a fluorophore) A, T, G, C, or U is an obvious approach, it will give rise to background staining, as these nucleotides could be incorporated not only in the rolling circle replication product but also elsewhere in the sample. Incorporating one or more artificial nucleotides, such as isoC or isoG, into the sequence of the probe and providing the complementary nucleotide as a labelled nucleotide (e.g. a fluorophore) during replication may therefore be preferable. Since such artificial nucleotides are not found in nature, iso-dCTP and iso-dGTP will not be incorporated elsewhere in the sample, minimizing background reactions. This aspect makes the use of a fluorophore-coupled iso-dCTP nucleotides or iso-dGTP nucleotides preferable. If detection is obtained through synthesis, the identifier element, defining the specific probe, may therefore preferably be one or more artificial nucleotide. Thus, in another embodiment, the invention relates to an element defining the specific probe, which is composed of one or more artificial nucleotides, such as e.g. 1-20 artificial nucleotides, or such as e.g. 1-10 artificial nucleotides, or such as e.g. 1-5 artificial nucleotides, or such as e.g. 4 artificial nucleotides, or such as e.g. 3 artificial nucleotides, or such as e.g. 2 artificial nucleotides, or such as e.g. 1 artificial nucleotide.

The total length of the probe may vary depending on the specific length of each element defined above. It can also be an advantage to use a probe which is as short as possible (without compromising the hybridization events and the rolling circle efficiency dramatically), since the shorter the circle, the more times the identifier element will be copied per unit length of DNA synthesized, increasing the detection signal at the end of the reaction. Thus, in one embodiment, the invention refers to a circular nucleic acid probe, wherein the total length of the probe is 30-200 nucleotides, such as e.g. 30-150 nucleotides, or such as e.g. 50-150 nucleotides, or such as e.g. 70-150 nucleotides, or such as e.g. 90-150 nucleotides, or such as e.g. 70-130 nucleotides, or such as e.g. 70-110 nucleotides.

Thus, in one embodiment, the invention relates to a probe comprising the sequence (SEQ ID NO:1):

5'-P-GTCGATCCCCTCAATGCACATGTTTGGCTCCAAAACATGCGGACC
ACCAGCTGGTACTTGACCGGATCGACTCGGAATAACCGA-3' wherein P is a 5'-phosphate.

Thus, in another embodiment, the invention relates to a probe comprising the sequence (SEQ ID NO:2):

5'-P-GTCGATCCCCTCAATGCACATGTTTGGCTCCAAAAATAGCGGACA
AGCCGAATACCCTTCTCCCGGATCGACTCGGAATAACCGA-3' wherein P is a 5'-phosphate.

Thus, in another embodiment, the invention relates to a probe comprising the sequence (SEQ ID NO:3):

5'-P-GTCGATCCCCTCAATGCTGCTGCTGTACTACAAAACATGCGGACC
ACCAGCTGGTACTTGACCGGATCGACTCGGAATAACCGA-3' wherein P is a 5'-phosphate.

Thus, in another embodiment, the invention relates to a probe comprising the sequence (SEQ ID NO:4):

5'-P-GTCGATCCCCTCAATGCTGCTGCTGTACTACAAAAATAGCGGACA
AGCCGAATACCCTTCTCCCGGATCGACTCGGAATAACCGA-3' wherein P is a 5'-phosphate.

Thus in another embodiment, the invention relates to a probe comprising the sequence (SEQ ID NO:5):

5'-P-GTCGATCCCCTCAATGCTGCTGCTGTACTACGCATGTGTGAGCCG
AGTCCTGGGTGCACGTCCCACAGCTCGGATCGACTCGGAATAACCGA-3' wherein P is a 5'-phosphate.

Thus in one embodiment the method refers to a nucleic acid probe, for use in rolling circle replication.

The probes mentioned above could be amplified using a nicking cassette. Since the ligation efficiency of probes amplified by the method of the invention is superior to chemically synthesised oligonucleotides, the probes of the invention are suited for the production of such probes.

Preferably, the nucleic acid probe according to invention is intended for use in the method of the invention.

In a second aspect of the invention, the invention relates to a method for amplifying an oligonucleotide contained within a probe comprising a suicide cassette, and furthermore releasing it from the suicide cassette at the end of the amplification. As mentioned above, a suicide cassette is a nicking cassette further comprising one or more restriction sites. Thus, in one embodiment, the invention relates to a method wherein the nicking cassette further comprises one or more restriction sites. It is to be understood that all suicide cassettes can be used as nicking cassette, by using the method described above.

The method using a suicide cassette comprises:

A method for amplifying one or more oligonucleotides comprising
  a) creating a nucleic acid probe (A) comprising one or more oligonucleotides and one or more nicking cassettes, and
  b) circularising of the probe (A), and
  c) providing a primer with a target sequence in part of said probe (A), and
  d) effecting rolling circle replication of said probe (A), and
  e) nicking of the rolling circle product of probe (A) within the one or more nicking cassettes obtaining multiple copies of a probe (B) complementary to the probe (A),
  f) circularising of the probe (B), and
  g) providing a primer with a target sequence in part of said probe (B), and
  h) effecting rolling circle replication of said probe (B), and
  i) nicking of the rolling circle product of probe (B) within the one or more nicking cassettes obtaining multiple copies of a probe (A) complementary to the probe (B).

For increasing the amount of product, steps b-i can be repeated as many times as needed. If each round e.g. amplifies 300×, two rounds equals $300^2$× amplification, three rounds equals $300^3$× amplification and four rounds equals $300^4$× amplification. Thus, after four rounds 1 ng of probe (A) may be turned into about 7 grams of probe (A), enough for several million individual application reactions. Obviously, the larger production of oligonucleotides occurs in the later cycles, so for large scale production the reaction is cycled more than once.

In one embodiment, the method according to the invention relates to a method, wherein steps b-i are performed one or more times, such as e.g. 1-100 times, or such as e.g. 1-50 times, or such as e.g. 1-25 times, or such as e.g. 1-10 times, or such as e.g. 1-5 times, or such as e.g. 1-4 times, or such as e.g. 1-3 times, or such as e.g. 1-2 times. In another embodiment, the method according to the invention relates to a method, wherein steps b-i are performed one or more times, such as e.g. one time, or such as e.g. two times, or such as e.g. three times, or such as e.g. four times, or such as e.g. five times, or such as e.g. six times, or such as e.g. seven times, or such as e.g. eight times, or such as e.g. nine times, or such as e.g. ten times.

The nucleic acid probe of the invention comprises the one or more oligonucleotides to be amplified by the method of the invention and one or more suicide cassettes, wherein the suicide cassette is a nucleic acid sequence comprising one or more complementary sequences, enabling parts of the suicide cassette to hybridise to parts of itself. This makes it possible for the probe of the invention to circularise by self-templated ligation. The suicide cassette is furthermore able to bind two or more modifying enzymes, preferably nicking enzymes and restriction enzymes. This allows the suicide cassette to be eliminated from the probe at the end of the reaction, thereby releasing the one or more amplified oligonucleotides. Therefore, the method of the invention provides production of oligonucleotides with freely designable 5'-ends and 3'-ends, of any lengths, at least 10-1000 nucleotides, and in amounts that are largely limited by the number of rounds of ligation, rolling circle replication, and nicking. Thus, in one embodiment, the invention relates to a nucleic acid probe comprising one or more suicide cassettes, wherein said one or more suicide cassettes are a nucleic acid sequence comprising one or more complementary sequences, one or more nicking sites and one or more restriction sites.

The purpose and characteristics of the suicide cassette are outlined in details below.

The Suicide Cassette

The suicide cassette of the invention is a nucleic acid sequence. The suicide cassette can comprise any sequence of the natural nucleotides G, C, A, T, I, U, or any artificial nucleotides e.g., but not limited to, iso-dCTP, iso-dGTP or a mixture thereof.

The suicide cassette of the invention has a single stranded length of 20-200 nucleotides. Thus, in one aspect, the invention relates to a method, wherein the one or more suicide cassettes has a length of 20-200 nucleotides, such as e.g. 20-150 nucleotides, or such as e.g. 20-100 nucleotides, or such as e.g. 20-80 nucleotides, or such as e.g. 20-60 nucleotides, or such as e.g. 20-40 nucleotides, or such as e.g. 20-30 nucleotides.

The aim of the suicide cassette is to enable amplification of an oligonucleotide by applying the method of the invention, which is based on the principle of rolling circle replication. The suicide cassette is added to the sequence of the oligonucleotide to be amplified before the initiation of the rolling circle replication, most conveniently during the initial synthesis of probe (A). At the end of the reaction, the suicide cassette is released from the amplified oligonucleotides by cutting the rolling circle product with a restriction enzyme. Thus, the suicide cassette is attached to the sequence of the oligonucleotide to be amplified during the steps of the rolling circle replication. At the end of the amplification reaction, the suicide cassette is eliminated from the sequence of the oligonucleotide.

Figure 3:
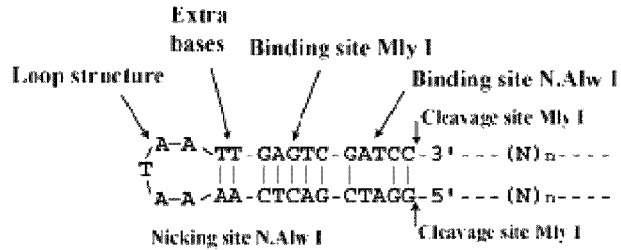
Figure 3:
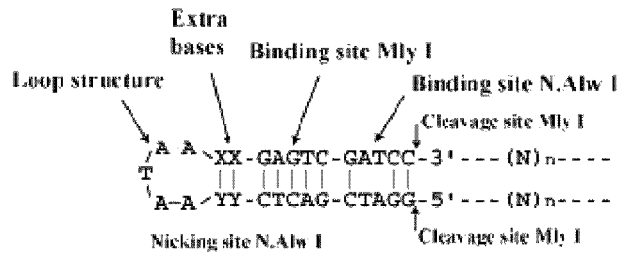
Figure 3:
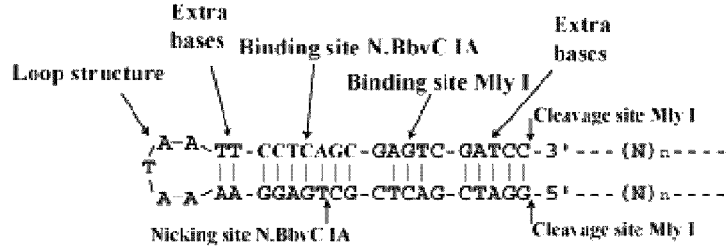
Figure 3:
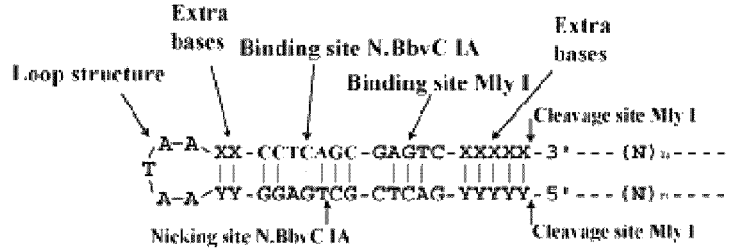

The suicide cassette possesses several characteristics: 1) the cassette comprises one or more complementary sequences, enabling the cassette to hybridise to itself, 2) the cassette comprises one or more sites for nicking enzymes, 3) the cassette comprises one or more restriction sites for restriction enzymes, and 4) the cassette comprises a loop structure (FIG. 3).

The different characteristics of the suicide cassette are described below:

Loop Structure of the Suicide Cassette

The loop structure of the suicide cassette aims to connect the ends of the two complementary sequences. The loop comprises 3-100 nucleotides, such as e.g. 3-80 nucleotides, or such as e.g. 3-60 nucleotides, or such as e.g. 3-40 nucleotides, or such as e.g. 3-20 nucleotides, or such as e.g. 3-10 nucleotides, or such as e.g. 3-9 nucleotides, or such as e.g. 3-8, or such as e.g. 3-7 nucleotides, or such as e.g. 3-6 nucleotides, or such as e.g. 3-5 nucleotides. Preferably, the loop sequence is 3-7 nucleotides long (FIG. 3), such as e.g. 3 nucleotides, or such as e.g. 4 nucleotides, or such as e.g. 5 nucleotides, or such as e.g. 6 nucleotides, or such as e.g. 7 nucleotides. Examples of loop structures include, but not limited to: 5'-AATAA-3' for the (+)-strand and 5'-TTATT-3' for the (−)-strand, 5'-GAA-3' for the (+)-strand and 5'-TTC-3' for the (−)-strand, 5'-GAAA-3' for the (+)-strand and 5'-TTTC-3' for the (−)-strand, or 5'-AAAA-3' for the (+)-strand and 5'-TTTT-3' for the (−)-strand. The (+)-strand is the loop-sequence of probe (A), while the (−)-strand is the loop-sequence of probe (B). The loop structure can be selected from but is not limited to the group consisting of AATAA, GAA, GAA, AAAA, and TTTT for the (+)-strand. Thus, in one embodiment, the invention relates to a method, wherein the one or more suicide cassettes comprise a loop-structure selected from the group consisting of AATAA, GAA, GAA, AAAA, and TTTT. This means that the sequence of the suicide cassette in probe (A) is selected from but not limited to the group consisting of AATAA, GAA, GAA, AMA, and TTTT. If a strong hairpin in the loop structure is needed, it is recommendable to have 5'-GAM-3' or 5'-GM-3' in the loop, as these two sequences are known to increase the melting temperature for a hairpin considerably (Hirao I et al. Nucleic Acids Res. 17(6), 2223-31 (1989) and Hirao I et. al Nucleic Acids Res. 22(4), 576-82 (1994)).

Complementary Sequences of the Suicide Cassette

The complementary sequences of the suicide cassette are positioned on each side of the loop structure in the sequence of the suicide cassette (FIG. 3). The complementary sequences comprise 10-100 nucleotides, such as e.g. 10-80 nucleotides, 10-60 nucleotides, 13-30 nucleotides or 13-40 nucleotides. Preferably, the complementary sequences are 12-20 nucleotides long, such as e.g. 12-20 nucleotides, such as e.g. 13-20 nucleotides, such as e.g. 14-20 nucleotides, or such as e.g. 15-20 nucleotides. Examples of complementary sequences are, but not limited to:

```
5'-XXCCTCAGCGAGTCXXXXX-3'
and

5'-YYYYYGACTCGCTGAGGYY-3',

5'-XCCTCAGCGAGTCXXXXX-3'
and
```

-continued

```
5'-YYYYYGACTCGCTGAGGY-3',
and

5'-XXGAGTCGATCC-3'
and

5'-GGATCGACTCYY-3'
``` wherein X and Y are any pair of natural or artificial nucleotides which can hybridize to each other.

In one embodiment, the invention relates to a method, wherein the one or more nicking cassettes comprise the complementary sequences:

```
5'-XXCCTCAGCGAGTCXXXXX-3'
and

5'-YYYYYGACTCGCTGAGGYY-3'
``` wherein X and Y are any pair of natural or artificial nucleotides which can hybridize to each other.

In a second embodiment, the invention relates to a method, wherein the one or more nicking cassettes comprise the complementary sequences:

```
5'-XCCTCAGCGAGTCXXXXX-3'
and

5'-YYYYYGACTCGCTGAGGY-3'
``` wherein X and Y are any pair of natural or artificial nucleotides which can hybridize to each other.

In a third embodiment, the invention relates to a method, wherein the one or more nicking cassettes comprise the complementary sequences:

```
5'-XXGAGTCGATCC-3'
and

5'-GGATCGACTCYY-3'
``` wherein X and Y are any pair of natural or artificial nucleotides which can hybridize to each other.

The aim of the complementary sequences of the suicide cassette is to form binding sites for both nicking enzymes and restriction enzymes. Furthermore, the complementary sequences enable the probe (A) or (B) to be circularized by self-templated hybridization of the complementary sequences in the suicide cassette.

Preferably, parts of the suicide cassette will be added to each end of the oligonucleotide sequence to be amplified during the initial synthesis. Preferably, a minimum of 5 nucleotides able to accommodate self-templated hybridization is positioned at each end of the oligonucleotide. Alternatively, the suicide cassette is positioned central in the probe (A). In this case circularisation can be performed by externally templated ligation.

Binding site for the nicking enzyme and restriction enzyme in the suicide cassette The suicide cassette comprises a recognition site for a nicking enzyme and a recognition site for a restriction enzyme.

As outlined in the definitions, a nicking enzyme recognises a double stranded nucleic acid sequence and cuts one and only one strand in the double stranded nucleic acid sequence, creating a 3'-hydroxyl and a 5'-phosphate. The nicking enzyme is used in step e) and in step i) of the method of the invention. In step e) the rolling circle product of the first amplification round comprising multiple copies of the complementary sequence to probe (A) (probe (B)) is exposed to the nicking enzyme. The amplified product comprises a multimer of successive copies of probe (B) and the suicide cassette. Each suicide cassette sequence is forming a hairpin as the complementary sequences in the suicide cassette are hybridising to each other. The nicking enzyme recognises the nicking site in the double stranded hairpin region of the suicide cassette and cuts one strand in the double stranded sequence. Thus, the cutting of the amplified product by the nicking enzyme results in multiple copies of probe (B). Thereby, the nicking enzyme prepares the rolling circle product of the first amplification round for the second round of ligation, rolling circle replication and cleavage/nicking. In step i) the rolling circle product of the second amplification round, comprising multiple copies of the complementary sequence to the probe (B) (probe (A)), is exposed to the nicking enzyme. The cutting of the amplified product of the second amplification round by the nicking enzyme results in multiple copies of probe (A). Thereby, the nicking enzyme prepares the rolling circle product of the second amplification round for additional rounds of rolling circle replication (step b) to step i) of the method of the invention).

A restriction enzyme recognises a double stranded nucleic acid sequence and cuts both strands in a double stranded nucleic acid sequence. The restriction enzyme can be used following steps d) or h) of the method of the invention. Following these steps, the rolling circle products comprise multiple copies of probe (A) or probe (B). As described above, each suicide cassette in the amplification product is forming a hairpin, as the complementary sequences in the suicide cassette are hybridising to each other. The restriction enzyme recognises the restriction site within the hairpin, and cleaves the DNA at a specific position, releasing the oligonucleotide contained within probe (A) or probe (B) from the suicide cassette. Thereby, multiple copies of the oligonucleotide contained within probe (A) or probe (B) are obtained.

Thus, in one embodiment, the invention relates to a method, wherein probe (A) is acquired after step h) by cutting the rolling circle product of probe (B) with a restriction enzyme.

In a second embodiment, the invention relates to a method, wherein probe (B) is acquired after step d) by cutting the rolling circle product of probe (A) with a restriction enzyme.

Preferably, the binding site for the restriction enzyme is positioned closest to the loop of the suicide cassette and the binding site for the nicking enzyme is furthest away from the loop (FIG. 3, A-B). Alternatively the binding site for the nicking enzyme is closest to the loop (FIG. 3, C-D), or the two binding sites are overlapping.

Additional base pairs next to the loop structure may be included to increase the cleavage efficiency of the enzymes (FIG. 3). Preferably, two base pairs are inserted, alternatively 0-50 base pairs are inserted, such as e.g. 0-40 base pairs, or such as e.g. 0-30 base pairs, or such as e.g. 0-20 base pairs, or such as e.g. 0-10 base pairs, or such as e.g. 0-8 base pairs, or such as e.g. 0-6 base pairs, or such as e.g. 0-4 base pairs.

Alternatively, 0-50 base pairs can be positioned between the two binding sites. If the recognition site for the type IIS restriction enzyme Mly I is positioned furthest away from the loop structure, an additional five base pairs are needed for the unrestricted design of the 5'-end and the 3'-end of the oligonucleotide to be amplified (FIG. 3, C-D).

In general, the extra base pairs can be freely chosen as long as they are not identical to the enzyme binding sites already used, or create additional binding sites for the enzymes to be used.

At the moment a limited number of nicking enzymes and restriction enzymes cutting blunt end outside its recognition sequence are available on the market, and therefore only a few suicide cassettes can be designed. In the future, nicking enzymes with higher cleavage efficiencies and more narrow recognition sites, as well as further restriction enzymes cleaving blunt end outside the recognition site (type IIS), will most likely be developed. This will allow new designs of suicide cassettes, possibly limiting the size of the suicide cassette and/or increasing the amplification efficiency.

The detailed structure of the suicide cassette may vary, as the position of the binding site for the nicking enzyme, the position of the binding site for the restriction enzyme, the number of extra nucleotides, and the nucleotide composition of the loop all can be adjusted for optimal performance in the amplification reaction. The sequences of the binding sites for the restriction enzyme and the nicking enzyme also depend on the specific enzymes used.

As an alternative to using the suicide cassette for self-templated ligation, the circularisation of probe (A) in the step b) can be obtained by externally templated ligation of one or more oligonucleotides.

Examples of nucleic acid sequences of the suicide cassette include, but are not limited to:

```
5'-GGATCGACTCYYAATAAXXGAGTCGATCC-3' (FIG. 3B),

5'-GGATCGACTCAAAATAATTGAGTCGATCC-3' (SEQ ID NO: 6)
(FIG. 3A),

5'-GGATCGACTCGCTGAGGYYAATAAXXCCTCAGCGAGTCGATCC-3'
(FIG. 3D),
and

5'-GGATCGACTCGCTGAGGAAAATAATTCCTCAGCGAGTCGATCC-3'
(SEQ ID NO: 7) (FIG. 3C)
``` wherein X and Y are any pair of natural or artificial nucleotides which can hybridize to each other.

In one aspect, the invention relates to a method, wherein the one or more nicking cassettes comprise a nucleic acid sequence selected from the group consisting of

```
5'-GGATCGACTCYYAATAAXXGAGTCGATCC-3',
                                              (SEQ ID NO: 6)
5'-GGATCGACTCAAAATAATTGAGTCGATCC-3',

5'-GGATCGACTCGCTGAGGYYAATAAXXCCTCAGCGAGTCGATCC-3',
and
                                              (SEQ ID NO: 7)
5'-GGATCGACTCGCTGAGGAAAATAATTCCTCAGCGAGTCGATCC-3'
``` wherein X and Y are any pair of natural or artificial nucleotides which can hybridize to each other.

In the following the different steps in the method of the invention are described in detail:

The one or more oligonucleotides to be amplified by the method of the invention can be any nucleic acid sequence comprising a sequence of at least 10-1000 nucleotides. Thus in one aspect, the invention relates to a method, wherein the one or more oligonucleotides comprise a sequence of 10-1000 nucleotides, such as e.g. 10-800 nucleotides, or such as e.g. 10-600 nucleotides, or such as e.g. 10-500 nucleotides, or such as e.g. 15-400 nucleotides, or such as e.g. 15-300 nucleotides, or such as e.g. 20-250 nucleotides, or such as e.g. 20-200, or such as e.g. such as e.g. 20-180, or such as e.g. 20-160, or such as e.g. 25-140 nucleotides, or such as e.g. 30-130 nucleotides, or such as e.g. 40-120 nucleotides, or such as e.g. 50-110 nucleotides, or such as e.g. 60-110 nucleotides, or such as e.g. 70-100 nucleotides.

The oligonucleotide can comprise any nucleic acid sequence composed of any of the natural deoxyribonucleotides G, C, A, T, I, U, and any of the artificial nucleotides, iso-dCTP, iso-dGTP or any natural or artificial nucleotides containing modifications. Preferably, the invention relates to a method, wherein the one or more oligonucleotides are DNA sequences.

In the case where artificial base pairs, such as iso-dCTP, iso-dGTP, or both, are included in the oligonucleotide to be amplified, or in the nicking cassette, the genetic alphabet is expanded to contain three base pairing components; G-C, A-T, and e.g. isoG-isoC.

Creation of Probe (A) (Step a)

The starting nucleic acid sequence (probe (A)), which comprises one or more oligonucleotides to be amplified, and one or more suicide cassettes, can be synthesised by standard chemical methods, such as e.g. beta-cyanoethyl phosphoramidite chemistry. The 5'-phosphate can be added during this synthesis, alternatively the 5'-phosphate can be coupled enzymatically to the 5'-end of the nucleic acid sequence, e.g. using the T4 polynucleotide kinase.

In one embodiment, the invention relates to a method, wherein probe (A) comprises the nucleic acid sequence (SEQ ID NO:8):

```
5'-P-GTCGATCCCTGCCATCTTAACAAACCCTCGACCTCAATGCTGCTG

CTGTACTAC-TCTTATGCGATTACCGGGCTGGATCGACTCGGAATTTCTT

CCGA-3'
``` wherein P is the 5'-phosphate.

Long sequences can be constructed by externally templated ligation of several synthesized sequences when the oligonucleotide to be amplified is very long e.g. 200-1000 nucleotides. In this situation, probe (A) can be created by externally templated ligation of two or more oligonucleotides (FIG. 5). In one embodiment, the invention relates to a method, wherein the probe (A) is created by ligation of one or more nucleic acid sequences comprising one or more parts of the one or more oligonucleotides and the one or more suicide cassettes.

Preferably, the probe (A) will contain a part of the suicide cassette in each end of the probe. Alternatively, the suicide cassette is positioned centrally in the oligonucleotide. If the probe (A) is created by externally templated ligation of several synthesized sequences, a part of the suicide cassette can be positioned at the 3'-end of one sequence and another part can be positioned in the neighboring 5'-end of another sequence. Alternatively, the cassette can be positioned centrally in one or more of the synthesized sequences. The start nucleic acid sequence (probe (A)) can also contain more than one suicide cassette, which can be either identical or different in design, i.e. nucleic acid composition.

In one aspect, the invention relates to a method, wherein the probe (A) comprises a nucleic acid sequence selected from the group consisting of:

```
5'-P-TCGATCC-Z-GGATCGACTCYYAATAAXXGAG-3',

5'-P-TCGATCC-Z-GGATCGACTCAAAATAATTGAG-3',

5'-P-CGAGTCGATCC-Z-GGATCGACTCGCTGAGGYYAATAAXXCCTCA
G-3',
``` and

5'-P-CGAGTCGATCC-Z-GGATCGACTCGCTGAGGAAAATAATTCCTCAG-3' wherein

Z is the one or more oligonucleotides to be amplified,

X and Y are any pair of natural or artificial nucleotides which can hybridize to each other, P is a 5'-phosphate.

Circularisation of Probe (A) (Step b)

Circularisation of probe (A) can be performed by self-templated ligation, by externally templated ligation, or by a combination of both. In case probe (A) contains a part of the suicide cassette in each end of probe (A), ligation can be performed by self-templated ligation (FIG. 5A). As seen in FIG. 5A, by hybridization between element 1A-1B and element 2A-2B, the nucleic acid probe folds into an open circle by self-templated hybridization. If the suicide cassette is positioned centrally in an oligonucleotide, ligation can be performed by externally templated ligation of one or more oligonucleotide (FIG. 5B). For long oligonucleotides, probe (A) can be constructed by ligation of more than one nucleic acid sequence, e.g. by a combination of self-templated hybridisation and externally templated hybridisation (FIG. 5C). Thus, in one embodiment, the invention relates to a method, wherein the closed circular structure of nucleic acid probe (A) is obtained by self-templated ligation. As outlined above, the circularisation of probe (A) can be obtained by self-templated folding of the probe (A) via hybridisation of the complementary regions of the one or more suicide cassettes within the probe (A), to enable ligation of the ends of probe (A).

A closed circular structure can be created by standard enzymatic ligation for both externally templated ligation and self-templated ligation, by applying the correct buffer conditions together with the appropriate energy source (ATP or NAD+) and a ligase. Preferably the T4 DNA ligase is used. ATP is supplied in a concentration of 0.001-10 mM preferably 0.1-1 mM, T4 DNA ligase is supplied in a final concentration of 0.00025-0.1 Weiss unit/µl, preferably 0.0025-0.05 U/µl. Alternatively, other ligases such as Tsc ligase, Tth ligase, Ampligase and Taq ligase, can be used. Chemical ligation may also be used. A circle containing one or more suicide cassettes will typically comprise 50-1000 nucleotides, preferably 50-500 nucleotides.

Primer Structure

For a standard DNA polymerase, a primer is needed to start the rolling circle replication reaction. In general, a primer consists of 5-50 nucleotides and preferably of 7-15 nucleotides. The primer has to be complementary to part of the nucleic acid probe, preferably a part outside the suicide cassette, alternatively a part inside the suicide cassette.

Preferably, the primer is 100% complementary to the probe, alternatively nucleotides at the 5'-end of the primer is non-complementary to the probe, e.g. 1 nucleotide, 3 nucleotides, 5 nucleotides, 10 nucleotides, 25 nucleotides or 50 nucleotides. If a polymerase containing 3' to 5' exonuclease activity is used (e.g. Phi29 DNA polymerase), non-complementary nucleotides at the 3'-end of the primer can be present, e.g. 1 nucleotide, such as e.g. 3 nucleotides, such as e.g. 5 nucleotides, such as e.g. 10 nucleotides, such as e.g. 25 nucleotides or such as e.g. 50 nucleotides. Furthermore, mismatched nucleotides in the primer can be present, e.g. 1 nucleotide, such as e.g. 3 nucleotides, such as e.g. 5 nucleotides, such as e.g. 10 nucleotides or 25 nucleotides.

The primer can be synthesised by standard chemical methods (e.g. beta-cyanoethyl phosphoramidite chemistry). A primer can also contain modifications e.g., but not limited to, streptavidine, avidin, biotin, $^{32}P$, and fluorophores, or it may comprise artificial nucleotides such as, but not limited to, LNA, PNA, iso-dCTP, and iso-dGTP.

For correct annealing between circle and primer a molar ratio of 0.1-100 between circle and primer is mixed, preferably 0.8-1.2. It is to be understood that polymerases which do not need a primer can also be used by the method of the invention, in this case no primers are needed to start the rolling circle replication.

In one embodiment, the invention relates to a method, wherein the primer comprises the nucleic acid sequence (SEQ ID NO:9):

5'-GTAGTACAGCAGCAGCATTGAGG-3'

In a second embodiment, the invention relates to a method, wherein the primer comprises the nucleic acid sequence (SEQ ID NO:10):

5'-CCTCAATGCTGCTGCTGTACTAC-3'

For production purposes, an improvement of the procedure can be obtained by letting one or more reagents, e.g. the primers, in step c and/or step g of the method of the invention, be anchored to a solid support, thereby attaching the rolling circle product to a surface. This will make it easier to change buffer conditions, and improve washing between the different steps, thereby minimizing background. In one example, the primer can be coupled in the 5'-end to a solid support-a 5'-biotin labelled primer may e.g. be coupled to a streptavidine coated solid support including, but not limited to, PCR-tubes, ELISA plates, beads, plastic CDs (produced by the company Amic), and microscope slides. Introduction of coupling of the primer to a solid support allows stringent washing after each round of rolling circle replication to remove the rolling-circle-template, thereby leaving only the coupled rolling circle product. This will minimize the production of the "wrong" strand in the second round of rolling circle replication. Microfluidics solutions provide a set of platforms where reagents can be anchored and conditions can be changed all within one design. Besides the physical anchoring of reagents (e.g. primer, polymerase) microfluidics systems also provide means of confining reagents to defined compartments, permanently or transiently, without attaching them to a support, i.e. a non-physical anchoring. Either the primer, the nucleic acid circle, the polymerase, or the endonucleases may thus be attached to a solid support or otherwise confined spatially without seriously damaging the overall efficiency of the amplification reaction. In the case of the circle, the circle can be locked around a structure on the support allowing rolling of the circle but inhibiting the circle from diffusing away from the surface.

Thus, in one aspect, the invention relates to a method, wherein the primer in step c is immobilised on a solid support.

In another aspect, the invention relates to a method, wherein the primer in step g is immobilised on a solid support.

In a third aspect, the invention relates to a method, wherein nucleic acid circle is attached to a solid support or otherwise spatially confined.

In a fourth aspect, the invention relates to a method, wherein the polymerase is attached to a solid support or otherwise spatially confined.

In a fifth aspect, the invention relates to a method, wherein the endonucleases are immobilised on a solid support or otherwise spatially confined.

First Rolling Circle Replication

When a polymerase and deoxynucleotide triphosphates (dNTPs) are combined with a probe hybridized to a primer (primer 1) under correct buffer conditions, rolling circle replication can take place. The polymerase will start the polymerization from the 3'-end of the primer, using the circular probe as a rolling-circle-template. As the circular probe is endless, the rolling circle product will comprise a multimer complementary to the sequence of the circular probe. Preferably the polymerase is the Phi29 DNA polymerase. A final concentration of 0.001-2 units of phi29 polymerase (Fermentas) is used, preferably 0.05-1 unit is used. A final dNTP concentration of 0.005-10 mM, preferably 0.1-1 mM is used. Alternatively, other polymerases such as the T7 DNA polymerase, Sequenase Version 2.0 T7 DNA Polymerase and Bst DNA polymerase can be used. The incubation time should be between 10 minutes and 24 hours, preferably 30 minutes to 5 hours, at the temperature optimal for the polymerase of choice. For some of the polymerases addition of single stranded binding protein (SSB) strongly enhances the rolling circle activity. Since the Phi29 DNA polymerase is not enhanced by SSB, a concentration of 0 µg/µl SSB is preferably used. Alternatively a concentration of 0.001-0.2 µg/µl can be used.

The length of the rolling circle product is preferably between 500 and 500,000 nucleotides in length. The speed and duration of the elongation can be controlled by varying the concentrations of dNTP, polymerase, circle, primer and SSB. Furthermore, temperature and buffer conditions are adjustable.

Nicking of Rolling Circle Product

The rolling circle product, which comprises multiple copies of a complementary sequence to probe (A) (called probe (B)), will fold into distinct hairpins composed of the suicide cassettes. To turn the multimer into monomers without the loss of nucleotides, the multimer is cut with a nicking enzyme. The binding site of the nicking enzyme is positioned in the suicide cassette. The following nicking enzyme can be used N.Alw I (Nt.Alw I), N.BbvC IA (Nb.BbvC I), N.BbvC IB (Nt.BbvC I), Nt.BstNB I, Nb.Bpu10I or Nb.Bsm I. Thus, in one embodiment, the invention relates to a method, wherein the nicking enzyme is selected from the group consisting of N.Alw I (Nt.Alw I), N.BbvC IA (Nb.BbvC I), N.BbvC IB (Nt.BbvC I), Nt.BstNB I, Nb.Bpu10I and Nb.Bsm I. Preferably, the N.Alw I (Nt.Alw I) is in the method of the invention. Therefore, in a preferred embodiment, the invention relates to a method, wherein the nicking enzyme is N.Alw I (Nt.Alw I). Preferably the buffer mixture is adjusted to accommodate nicking conditions without a purification step, alternatively the rolling circle product is purified by known methods (e.g. gel purification or ethanol precipitation) and optimal buffer conditions for the nicking enzyme is supplied. Preferably 0.3-1 U/µl of nicking enzyme is used alternatively 0.05-3 U/µl is used. Incubation time can be from 30 minutes to 3 days, preferably 3-20 hours.

Second Ligation

To turn the nicked product into a closed circular structure, a denaturation-renaturation step by heating and cooling may be performed, which will promote the monomers (multiple copies of probe (B)) to fold into an open circular structure by self-templated hybridization in the region of the suicide cassette (FIG. 1). Thus, circularisation of probe (B) can be obtained by intra-molecular hybridization of the probe (B) via hybridisation of the complementary regions of the one or more suicide cassettes, enabling ligation of the ends of probe (B). Therefore, one embodiment of the invention relates to a method, wherein the circularisation of probe (B) is obtained by self-templated ligation.

A closed circle structure of probe (B) can be created by standard enzymatic ligation. Preferably, the buffer conditions are adjusted to improve ligation without a purification step, alternatively the nicked product is purified by known methods (e.g. gel purification or ethanol precipitation), before ligation.

Second Rolling Circle Replication

The second rolling circle replication is performed similarly to the first rolling circle replication. Preferably, the primer (primer 2) is complementary to the one used in the first round of rolling circle, alternatively it hybridizes to another part of the probe sequence than primer 1.

Optionally Nicking of the Rolling Circle Product of the Second Round

Yet another round of nicking can be performed to amplify the oligonucleotide further. The difference from the first round of nicking is that it is now a tandem repeat of probe (A), which is nicked and not a tandem repeat of probe (B). Thus, the probe (A) and probe (B) can be amplified further through successive rounds of ligation, rolling circle replication, and nicking before the removal of the suicide cassette.

Removing the Suicide Cassette

The suicide cassette enables the continuous copying of the nucleic acid sequence, such as e.g. DNA, through (+) and (−) strand syntheses. However, once the synthesized nucleic acid sequence, such as e.g. DNA, is going to be used for other purposes, e.g. as a hybridization probe, it may be desirable to remove the suicide cassette.

The product of the rolling circle reaction will fold into distinct hairpins formed by the suicide cassette. To turn the multimer into monomers, and at the same time remove the suicide cassette, the multimer is cut with a type IIS restriction enzyme. The binding site is positioned in the suicide cassette. The enzyme cuts in the suicide cassette, or at the border of the suicide cassette and the oligonucleotide, thereby releasing the oligonucleotide from the suicide cassette. Thus, in one embodiment, the invention relates to a method, wherein the restriction enzyme recognises the restriction site in the one or more nicking cassettes, said restriction enzyme cutting in the one or more nicking cassettes, or at the border of the one or more nicking cassettes and the one or more oligonucleotides.

In one embodiment, the invention relates to a method, wherein the restriction enzyme is a type IIS enzyme. Preferably, the restriction enzyme is Mly I, alternatively another restriction enzyme can be used. Therefore, in a preferred embodiment, the invention relates to a method, wherein the restriction enzyme is Mly I. Preferably, the buffer mixture is adjusted to improve cleavage conditions without a purification step. Alternatively, the rolling circle product is purified by known methods (e.g. gel purification or ethanol precipitation) before restriction cleavage, and optimal buffer conditions for the restriction enzyme is supplied. The incubation time can be from 30 minutes to 3 days, preferably 3-20 hours. If necessary, the enzyme can be heat-inactivated. Following restriction cleavage, the end product is purified e.g. by gel purification, ethanol precipitation or HPLC purification.

The Probe of the Invention

The invention also relates to a nucleic acid probe comprising one or more suicide cassettes, wherein said one or more suicides cassettes are nucleic acid sequences comprising one or more complementary sequences, one or more nicking sites and one or more restriction sites. As mentioned above, a suicide cassette is a nicking cassette further comprising a restriction site. Thus in one embodiment the invention relates to a nucleic acid probe, wherein the nicking cassette further comprises one or more restriction sites. The details of the complementary sequences, nicking sites and restriction sites are as outlined above.

Furthermore, the probe of the invention comprises one or more oligonucleotides for amplification by the method of the invention. Thus, the invention relates to a nucleic acid probe comprising one or more oligonucleotides and one or more suicide cassettes. As outlined above, the one or more oligonucleotides for amplification by the method of the invention comprise a sequence of at least 10-1000 nucleotides. Therefore, in one aspect, the invention relates to a nucleic acid probe, wherein the one or more oligonucleotides comprise a sequence of at least 10-1000 nucleotides.

As mentioned, the details of the complementary sequences, nicking sites and restriction sites for the suicide cassette comprised in the probe of the invention are as outlined under the method of the invention.

Therefore, in one embodiment, the invention relates to a nucleic acid probe, wherein the suicide cassette has a length of 20-200 nucleotides in its single stranded form.

In a second embodiment, the invention relates to a nucleic acid probe, wherein the suicide cassette comprises a loop-structure selected from the group consisting of AATAA, GAA, GAA, AAAA, and TTTT.

In a third aspect, the invention relates to a nucleic acid probe, wherein the suicide cassette comprises the complementary sequences:

5'-XXCCTCAGCGAGTCXXXXX-3'
and

5'-YYYYYGACTCGCTGAGGYY-3' wherein X and Y are any pair of natural or artificial nucleotides which can hybridize to each other.

In another embodiment, the invention relates to a nucleic acid probe, wherein the suicide cassette comprises the complementary sequences:

5'-XCCTCAGCGAGTCXXXXX-3'
and

5'-YYYYYGACTCGCTGAGGY-3' wherein X and Y are any pair of natural or artificial nucleotides which can hybridize to each other.

In yet another embodiment, the invention relates to a nucleic acid probe, wherein the suicide cassette comprises the complementary sequences:

5'-XXGAGTCGATCC-3'
and

5'-GGATCGACTCYY-3' wherein X and Y are any pair of natural or artificial nucleotides which can hybridize to each other.

In yet another embodiment, the invention relates to a nucleic acid probe, wherein the suicide cassette comprises a nucleic acid sequence selected from the group consisting of:

5'-GGATCGACTCYYAATAAXXGAGTCGATCC-3',

5'-GGATCGACTCAAAATAATTGAGTCGATCC-3', (SEQ ID NO: 6)

5'-GGATCGACTCGCTGAGGYYAATAAXXCCTCAGCGAGTCGATCC-3',
and (SEQ ID NO: 7)

5'-GGATCGACTCGCTGAGGAAAATAATTCCTCAGCGAGTCGATCC-3' wherein X and Y are any pair of natural or artificial nucleotides which can hybridize to each other.

In another aspect, the invention relates to a nucleic acid probe, wherein the probe comprises a nucleic acid sequence selected from the group consisting of:

5'-P-TCGATCC-Z-GGATCGACTCYYAATAAXXGAG-3',

5'-P-TCGATCC-Z-GGATCGACTCAAAATAATTGAG-3',

5'-P-CGAGTCGATCC-Z-GGATCGACTCGCTGAGGYYAATAAXXCCTCAG-3',
and

5'-P-CGAGTCGATCC-Z-GGATCGACTCGCTGAGGAAAATAATTCCTCAG-3' wherein

Z is the one or more oligonucleotides to be amplified,

X and Y are any pair of natural or artificial nucleotides which can hybridize to each other, P is a 5'-phosphate.

The nucleic acid probe of the invention can be used in rolling circle replication for different purposes.

For production purposes it may be desirable not to acquire the entire rolling circle product by restriction cleavage with Mly I, but leave a batch for further rounds of ligation-rolling circle replication-nicking.

Since the method of the invention offers the amplification of 5-phosphorylated oligonucleotides with freely designable 5'-ends and 3'-ends, an obvious production target could be padlock probes where the ligation efficiency of probes produced by the method of the invention is superior to chemically synthesized oligonucleotides.

Thus, in one embodiment, the method refers to a nucleic acid probe, eg. padlock probe for use in rolling circle replication.

Another obvious production target could be long oligonucleotides (at least 1000 nucleotides). Since chemical synthesis has a limitation in the range of 150 nucleotides, the method of the invention allows for the production of oligonucleotides with freely designable 5'-ends and 3'-ends at a length previously not possible. Such long oligonucleotides could be used for e.g. substrates for enzymatic reactions, for in situ hybridizations, etc.

Suicide/nicking cassettes can also be ligated to both ends of a PCR-product, a PCR-product wherein the ends have been modified with a restriction enzyme, or restriction cleaved DNA purified from an organism. In this way the one or more targets can be turned into closed circular structures. The closed circular structure can then serve for amplification of the DNA contained within the one or more cassettes, by the method outlined above. In a similar manner a single stranded sequence, e.g. cDNA, can be turned into a circular structure, by ligating a nicking/suicide cassette to the ends of the sequence. The closed circular structure can then serve for amplification of the DNA contained within the cassette, by the method outlined above.

Preferably, the nucleic acid probe according to invention is intended for use in the method of the invention.

CROSS-REFERENCE TO RELATED APPLICATIONS

This application claims priority from DK PA 2005 00521, filed on Apr. 12, 2005.

Each of these applications, patents, and each document cited in this text, and each of the documents cited in each of these applications, patents, and documents ("application cited documents"), and each document referenced or cited in the application cited documents, either in the text or during the prosecution of the applications and patents thereof, as well as all arguments in support of patentability advanced during prosecution thereof, are hereby incorporated herein by reference.

In addition, singular reference do not exclude a plurality. Thus, references to "a", "an", "first", "second" etc. do not preclude a plurality.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

As will be apparent, preferred features and characteristics of one aspect of the invention may be applicable to other aspects of the invention.

EQUIVALENTS

The invention may be embodied in other specific forms without departing from the spirit or essential characteristics thereof. The foregoing embodiments are therefore to be considered in all respects illustrative rather than limiting on the invention described herein. Scope of the invention is thus indicated be the appended claims rather than by the foregoing description, and all changes that come within the meaning and range of equivalency of the claims are intended to be embraced by reference therein.

The invention will hereinafter be described by way of the following non-limiting Figures and Examples.

EXAMPLES

Example 1

Amplification of the 66 Nucleotides Oligonucleotide SF86-SC by the Use of a Suicide Cassette By the use of the invention we were able to amplify an oligonucleotide approximately 100,000 fold. The invention uses a suicide cassette as a tool to amplify the specified oligonucleotide. A suicide cassette is a hairpin structure containing a binding site for a nicking enzyme and a restriction enzyme; in this example N.Alw I (Nt.Alw I) and Mly I respectively (FIG. 3, A-B). By having the suicide cassette positioned at each end of the originally synthesized oligonucleotide it is possible, by self-templated ligation, to turn the linear DNA sequence into a closed circular one. By successive rounds of rolling circle replication, nicking and ligation, the oligonucleotide can be amplified with either polarity. In the last step the suicide cassette can be separated from the oligonucleotide by restriction cleavage with Mly I (FIG. 1).

Oligonucleotide to be Amplified+Suicide Cassette (SF86) (SEQ ID NO:8):

5'-P-<u>GTCGATCCC</u>TGCCATCTTAACAAACCCTCGACCTCAATGCTGCTG

CTGTACTAC-TCTTATGCGATTACCGGGCT<u>GGATCGACTCGGAATTTCTT</u>

<u>CCGA</u>-3'

Underlined: Nucleotides which are part of the suicide cassette

Not underlined: Nucleic acid sequence to be amplified

Oligonucleotide to be Amplified without Suicide Cassette (SF86-SC) (SEQ ID NO:11):

5'-P-CTGCCATCTTAACAAACCCTCGACCTCAATGCTGCTGCTGTACTA

C-TCTTATGCGATTACCGGGCT-3'

Primer for First Round of Rolling Circle Replication ((+)-Primer) (SEQ ID NO:9):

5'-GTAGTACAGCAGCAGCATTGAGG-3'

Primer for Second Round of Rolling Circle Replication ((−)-Primer) (SEQ ID NO:10):

5'-CCTCAATGCTGCTGCTGTACTAC-3'

Cleavage Oligonucleotides for Bcc I (Bcc I (+)-Oligo) (SEQ ID NO:12)

5'-GTTTGTTAAGATGGCAG-3'

Cleavage Oligonucleotides for Bcc I (Bcc I (−)-Oligo) (SEQ ID NO:13)

5'-CTGCCATCTTAACAAAC-3'

Figure 4:
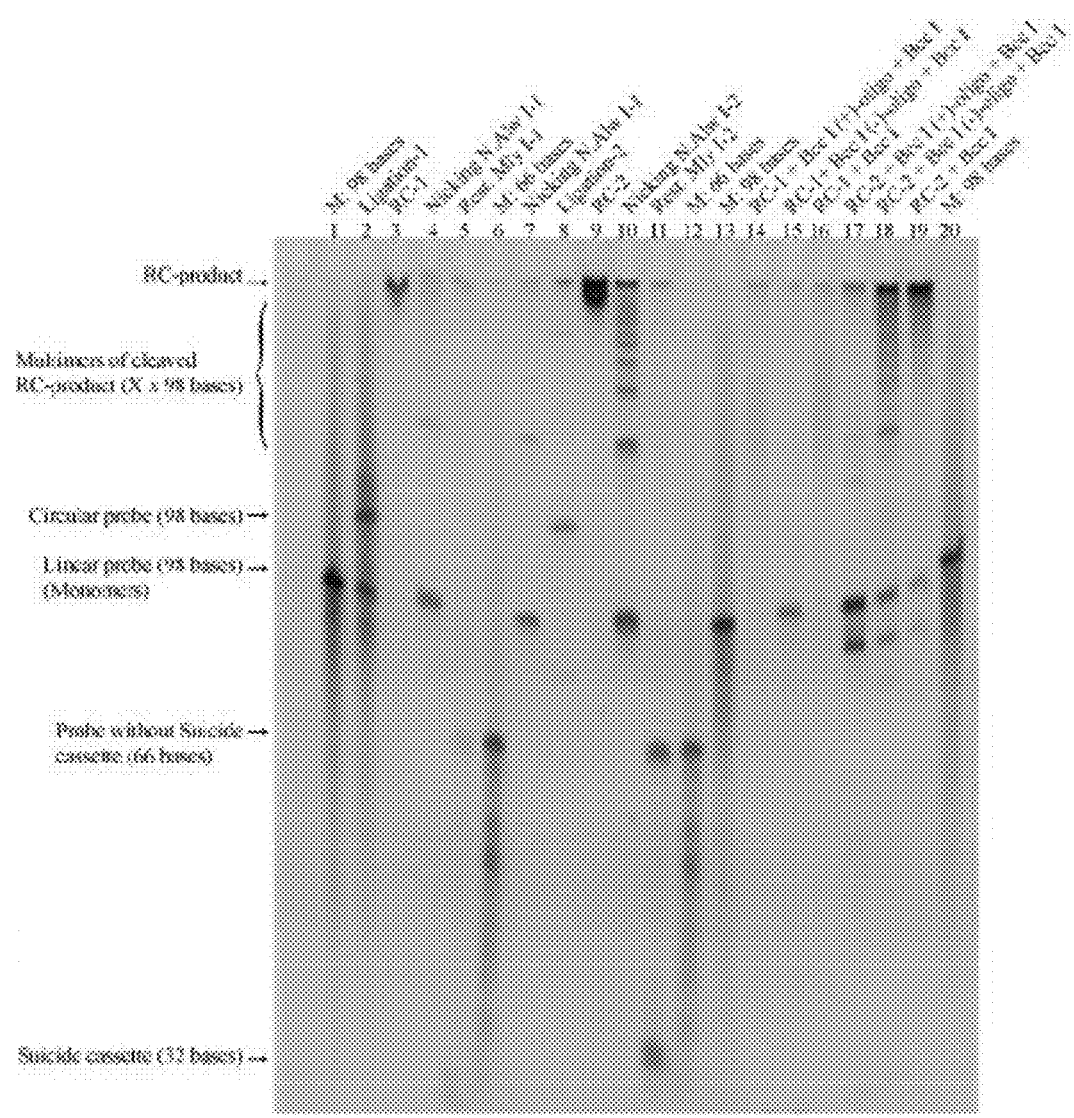

Step 1, ligation 1. Self-templated ligation was performed with 1.5 µM of SF86 and 0.0125 U/µl T4 DNA ligase (Fermentas) in the recommended buffer for 30 min at 37° C. (FIG. 1A-1B and FIG. 4 lane 1-2).

Step 2, Rolling circle replication 1. Rolling circle replication was initiated in a mixture containing 250 µM of the ligated product, 250 µM of (+)-primer, 0.25 µM dNTP, and 0.25 U/µl Phi29 DNA polymerase (Fermentas) in the recommended buffer for 16 hours at 37° C. (FIG. 1C and FIG. 4 lane 3). The product was a mulitimeric DNA sequence complementary to the DNA circle, which functioned as a rolling-circle-template.

Step 3, Nicking of RC-product 1. The RC-product was nicked adding one volume of 1×NEB-buffer 2 containing 1 U/µl N.Alw I (Nt.Alw I), and incubating for 16 hours at 37° C. By addition of N.Alw I (Nt.Alw I) the RC-product could be turned into monomers (FIG. 1D and FIG. 4 lane 4 and 7).

Step 4, ligation 2. By making a heat denaturation-renaturation step the monomers will predominantly fold into open circle structures ready for a second round of ligation (FIG. 1F). By the addition of T4 DNA ligase and ATP to final concentration of 0.05 U/µl and 0.5 µM, second round of ligation was performed (FIG. 1G and FIG. 4 lane 8). This reaction turns the monomers into a single stranded DNA circle comprising a hairpin. The circle is complementary to the circle made in step 1.

Step 5, Rolling circle replication 2. The ligation product was diluted 100× and an equal concentration of the (−)-primer (complementary to the primer used in step 2) was added. The second rolling circle replication was performed in a mixture 0.25 µM dNTP, and 0.25 U/µl Phi29 DNA polymerase (Fermentas) in the recommended buffer for 16 hours at 37° C.

(FIG. 1H and FIG. 4 lane 9). The product was a mulitimeric DNA sequence identical to SF86.

Step 6A, Cleavage with Mly I. The SF86-SC oligonucleotide could be separated from the suicide cassette by cleavage with Mly I (FIG. 1I). The reaction included the addition of 1 volume of 1×NEB-buffer 4 containing 1 U/µl of Mly I and incubation for 16 hours at 37° C. The products were isolated on a 10% denaturing polyacrylamid gel, separating the 5'-phosphorylated SF86-SC from the suicide cassette (FIG. 4 lane 11).

Step 6B, Nicking with N.Alw I (Nt.Alw I) 2. Alternatively, several rounds of nicking, ligation and rolling circle replication can be performed amplifying the oligonucleotide even further (FIG. 13 and FIG. 4 lane 10).

To evaluate the purity of the RC-products, the Bcc I (+)-oligo and the Bcc I (−)-oligo were hybridized to both the first and second round of RC-products. The hybridization sequence contain a binding site for the restriction enzyme Bcc I (NEB), which recognizes a non-palindromic sequence. After the first round of RC, a cleavage band only appeared in the lane where the Bcc I (−)-oligo, complementary to part of the expected sequence of the RC-product, was hybridized (FIG. 4 lane 15). By contrast, in the lanes where the Bcc I (+)-oligo was hybridized, or none was added, no cleavage bands appeared (FIG. 4 lane 14 and 16). This shows that the product of the first rolling circle replication reaction is pure and has one polarity.

After the second round of rolling circle replication, bands with the expected size appeared in the lanes containing both the Bcc I (+)-oligo, the Bcc I (−)-oligo and without a cleavage oligonucleotide (FIG. 4 lane 17-19). The cleavage band in the lane containing the Bcc I (+)-oligo is much more prominent and the amount of rolling circle product left in the gel-slot is much less than for the two other lanes, showing that the predominant product is the desired oligonucleotide. The background amplification seen in lanes 18 and 19 can be accounted for, by the fact that no purification was performed after the first round of rolling circle replication, leaving behind the circular probe from the first RC-reaction. In the second round of amplification, rolling circle products of both polarities will therefore be amplified. These products can hybridize to each other giving rise to the band in the lane where neither the Bcc I (+)-oligo nor the Bcc I (−)-oligo were hybridized. Most likely this co-amplification is the reason for the unexpected band seen in FIG. 4 lane 17-19. The reactions were performed by adding 1 volume of NEB-buffer 1 containing 1 U/µl of Bcc I and 1 µM of either the Bcc I (+)-oligo or the Bcc I (−)-oligo.

FIGURE LEGENDS

FIG. 1
Rolling Circle Replication of an Oligonucleotide by the Use of a Nicking Cassette which is a Suicide Cassette.

A) The (+) probe can fold into an open circle structure by self-templated hybridization. B) The (+) probe can be turned into a closed circle structure by self-templated ligation. C) The first rolling circle replication reaction is started by the addition of primer and polymerase. The rolling circle product will be a repeated sequence complementary to the (+) probe. D) If using a suicide cassette, optionally the multimer of the (−) probe can be cut with Mly I, thereby releasing the suicide cassette from the one or more oligonucleotides.

E) By applying a nicking enzyme, which binds and nicks the suicide/nicking cassette, the multimer is turned into monomers of the (−) probe. F) The (−) probe can fold into an open circle structure by self-templated hybridization. The (−) probe monomers will preferentially fold into open circular structures following a fast heat denaturation-renaturation step. G) The (−) probe can be turned into a closed circular structure by self-templated ligation. H) The second rolling circle replication reaction is started by the addition of primer and polymerase. The rolling circle product will be a repeated sequence complementary to the (−) probe. I) If using a suicide cassette, optionally the multimer of the (+) probe can be cut with Mly I, thereby releasing the suicide cassette from the one or more oligonucleotides. J) Further rounds of nicking-ligation-rolling circle replication can be performed if higher levels of amplification are desired, thereby returning to step A).

(+) denotes the sense strand, (−) denotes the antisense strand. The thin line of the sequence denotes the suicide cassette and the broad line of the sequence denotes the oligonucleotide to be amplified. It is to be understood that products of the (+) strand and the (−) strand with or without an attached cassette can be amplified using the construct as a suicide cassette or as a nicking cassette.

FIG. 2
Examples of the Nucleotide Sequence of the Nicking Cassette.

The nicking cassette is composed of the following elements: A binding site for a nicking enzyme, a loop, and additional base pairs. A: Nicking cassette containing the binding and cleavage site for N.BbvC IA (Nb.BbvC I). Top: Linear sequence. Bottom: Structure of the sequence. B: Nicking cassette containing the binding and cleavage site for N.BbvC IB (Nt.BbvC I). Top: Linear sequence. Bottom: Structure of the sequence. C: Nicking cassette containing the binding and cleavage site for N.Alw I (Nt.Alw I). Top: Linear sequence. Bottom: Structure of the sequence. D: Nicking cassette containing the binding and cleavage site for Nb.Bsm I. Top: Linear sequence. Bottom: Structure of the sequence. In example A-D a loop comprised of 5'-AATAA is used. $(N)_n$ denotes the oligonucleotide to be amplified, (↑) or (↓) denote cleavage sites for the nicking enzyme. (|) indicates base pairing. X and Y are any pair of natural or artificial nucleotides which can hybridize to each other FIG. 3
Examples of the Nucleotide Sequence of the Suicide Cassette.

The suicide cassette is composed of the following elements: A binding site for a nicking enzyme, a binding site for a restriction enzyme, a loop, and additional base pairs. A: The binding site for Mly I is positioned closest to the loop whereas the binding site for N.Alw I (Nt.Alw I) is positioned further away. Two additional base pairs are inserted. Top: Linear sequence. Bottom: Structure of the sequence. B: The binding site for Mly I is positioned closest to the loop, whereas the binding site for N.Alw I (Nt.Alw I) is positioned further away. Two additional random base pairs are inserted. Top: Linear sequence. Bottom: Structure of the sequence. C: The binding site for N.BbvC IA (Nb.BbvC I) is positioned closest to the loop, whereas the binding site for Mly I is positioned further away. Seven additional base pairs are inserted. Top: Linear sequence. Bottom: Structure of the sequence. D: The binding site for N.BbvC IA (Nb.BbvC I) is positioned closest to the loop, whereas the binding site for Mly I is positioned further away. Seven additional random base pairs are inserted. Top: Linear sequence. Bottom: Structure of the sequence. In A-D a loop comprised of 5'-AATAA is used. $(N)_n$ denotes the oligonucleotide to be amplified, (↑) and (↓) denote cleavage sites for restriction and nicking enzymes. (|) indicates base pairing. X and Y are any pair of natural or artificial nucleotides which can hybridize to each other.

FIG. 4

Gel Picture Showing the Amplification of the Oligonucleotide SF86-SC by the Use of a Suicide Cassette.

Lane 2) Circularization of oligonucleotide SF86 by self-templated ligation. Lane 3) Rolling circle product of diluted circle from lane 2, (+)-primer used. Lane 4 and 7) Nicking of RC-product from lane 3 with N.Alw I (Nt.Alw I). Lane 5) Restriction cleavage of RC-product from lane 3 with Mly I. Lane 8) Ligation of nicked product from lane 7 by self-templated ligation. Lane 9) Rolling circle product of the diluted circle from lane 8, (−)-primer used. Lane 10) Nicking of RC-product from lane 9 with N.Alw I (Nt.Alw I). Lane 11) Restriction cleavage of RC-product from lane 9 with Mly I. Lane 14) Hybridization of Bcc I (+)-oligo to RC-product from lane 3 and restriction cleavage with Bcc I. Lane 15) Hybridization of Bcc I (+)-oligo to RC-product from lane 3 and restriction cleavage with Bcc I. Lane 16) Restriction cleavage of RC-product from lane 3 with Bcc I. Lane 17) Hybridization of Bcc I (+)-oligo to RC-product from lane 9 and restriction cleavage with Bcc I. Lane 18) Hybridization of Bcc I (−)-oligo to RC-product from lane 9 and restriction cleavage with Bcc I. Lane 19) Restriction cleavage of RC-product from lane 9 with Bcc I. Lane 1, 13 and 20) 98 nucleotide marker. Lane 6 and 12) 66 nucleotide marker. RC-1: First round of rolling circle replication. RC-2: Second round of rolling circle replication. RC: Rolling circle. 10% denaturing polyacrylamid gel, stained with SYBR Gold.

FIG. 5

Different Ways of Making Circular Probes Containing Either a Suicide Cassette or a Nicking Cassette.

A) Self-templated hybridization. Hybridization of element 1A to 1B and element 2A to 2B induces an open circle conformation of the nucleic acid sequence. B) Externally templated hybridization. C) Combination of self-templated hybridization and externally templated hybridization. A-C) Following the hybridization steps, the nucleic acid sequences are in position to be ligated, thereby being turned into a closed circular structure. (|) denotes base pairing.

REFERENCES

US 2003/0087241
WO 97/20948
Dahl F et al., Proc Natl Acad Sci USA. 101(13), 4548-53 (2004)
Hirao I et al. Nucleic Acids Res. 17(6), 2223-31 (1989)
Hirao I et. al Nucleic Acids Res. 22(4), 576-82 (1994)
Larsson C. et al. *Nature Methods* 1, 227-32 (2004))
Masuda N. et al. Nucleic Acids Res. 15; 27(22) 4436-43 (1999)

The invention claimed is:

1. A method for amplifying one or more oligonucleotides, said method comprising the steps of
   a) providing a nucleic acid probe (A) comprising one or more oligonucleotides and one or more double stranded nicking cassette(s) having complementary sequences, each nicking cassette comprising a double stranded nicking endonuclease recognition site having complementary nucleic acid sequences, wherein a nicking endonuclease capable of recognising said double stranded recognition site generates a nick in only one of the strands of the double stranded nucleic acid,
   b) circularising probe (A) as provided in step a) by self-templated hybridisation of the complementary nucleic acid sequences of the one or more nicking cassette(s) and ligating said circularised probe (A),
   c) providing a primer capable of recognising a target sequence in part of said circularised probe (A) obtained in step b),
   d) using the primer provided in step c) to effect rolling circle replication of said circularised probe (A), thereby providing a rolling circle product of probe (A) comprising one or more double stranded nicking cassette(s) having complementary sequences, each nicking cassette comprising a double stranded nicking endonuclease recognition site having complementary nucleic acid sequences,
   e) providing a nicking endonuclease capable of recognising double stranded nicking endonuclease recognition sites in the rolling circle product of probe (A), and nicking said double stranded nicking endonuclease recognition sites with the provided nicking endonuclease, thereby obtaining multiple copies of a probe (B) comprising a nucleic acid sequence complementary to the probe (A),
   f) circularising probe (B) as obtained in step e) by self-templated hybridisation of the complementary nucleic acid sequences of the one or more nicking cassette(s) and ligating said circularised probe (B) comprising a nucleic acid sequence complementary to the probe (A),
   g) providing a primer capable of recognising a target sequence in part of said circularised probe (B) obtained in step f),
   h) using the primer provided in step g) to effect rolling circle replication of said circularised probe (B), thereby providing a rolling circle product of probe (B) comprising one or more double stranded nicking cassette(s) having complementary sequences, each nicking cassette comprising a double stranded nicking endonuclease recognition site having complementary nucleic acid sequences, and
   i) providing a nicking endonuclease capable of recognising double stranded nicking endonuclease recognition sites in the rolling circle product of probe (B), and nicking said double stranded nicking endonuclease recognition sites with the provided nicking endonuclease, thereby obtaining multiple copies of a probe (A) comprising a nucleic acid sequence complementary to the probe (B).

2. The method of claim 1, wherein amplification of probes (A) and (B) is achieved by repeating steps b) to i) one or more times.

3. The method of claim 1, wherein amplification of probes (A) and (B) is achieved by repeating steps b) to i) more than once.

4. The method of claim 2, wherein probe (A) is obtained after step i) in each synthesis round.

5. The method of claim 2, wherein probe (B) is obtained after step e) in each synthesis round.

6. The method of claim 2, wherein oligonucleotides having a length of up to 1000 nucleotides are amplified.

7. The method of claim 1, wherein the one or more oligonucleotides are DNA oligonucleotides.

8. The method of claim 1, wherein the nicking enzyme is selected from the group consisting of N.Alw I (Nt.Alw I), N.BbvC IA (Nb.BbvC I), N.BbvC IB (Nt.BbvC I) and Nb.Bsm I.

9. The method of claim 1, wherein the nicking enzyme is N.Alw I (Nt.Alw I).

10. The method of claim 1, wherein the primer in step c) is immobilised on a solid support.

11. The method of claim 1, wherein the primer in step g) is immobilised on a solid support.

12. The method of claim 1, wherein the one or more oligonucleotides comprise a sequence of from 10 to 1000 nucleotides.

13. The method of claim 1, wherein the one or more nicking cassette(s) have a length of from 20 to 200 nucleotides.

14. The method of claim 1, wherein the one or more nicking cassettes comprise a loop-structure selected from the group consisting of AATAA, GAA, GAAA, AAAA, and TTTT.

15. The method of claim 1, wherein the one or more nicking cassettes comprise the complementary sequences:

```
5'-XXGCTGAGGXX-3'                    (SEQ ID NO: 17)
and

5'-YYCCTCAGCYY-3',                   (SEQ ID NO: 18)
``` wherein X and Y are any natural or artificial nucleotide which can hybridize to each other.

16. The method of claim 1, wherein the one or more nicking cassettes comprise the complementary sequences:

```
5'-XXCCTCAGCXX-3'                    (SEQ ID NO: 19)
and

5'-YYGCTGAGGYY-3',                   (SEQ ID NO: 20)
``` wherein X and Y are any pair of natural or artificial nucleotides which can hybridize to each other.

17. The method of claim 1, wherein the one or more nicking cassettes comprise the complementary sequences:

```
5'-XXXXXXXGATCCXX-3'                 (SEQ ID NO: 21)
and

5'-YYGGATCYYYYYYY-3',                (SEQ ID NO: 22)
``` wherein X and Y are any pair of natural or artificial nucleotides which can hybridize to each other.

18. The method claim 1, wherein the one or more nicking cassettes comprise the complementary sequences:

```
5'-XXGAATGCXX-3'                     (SEQ ID NO: 23)
and

5'-YYGCATTCYY-3'                     (SEQ ID NO: 24)
``` wherein X and Y are any pair of natural or artificial nucleotides which can hybridize to each other.

19. The method of claim 1, wherein the one or more nicking cassettes comprise a nucleic acid sequence selected from the group consisting of:

```
                                     (SEQ ID NO: 25)
5'-YYCCTCAGCYYAATAAXXGCTGAGGXX-3', (SEQ ID NO: 26)
5'-YYGCTGAGGYYAATAAXXCCTCAGCXX-3', (SEQ ID NO: 27)
5'-YYGGATCYYYYYYYAATAAXXXXXXXGATCCXX-3'
and (SEQ ID NO: 28)
5'-YYGAATGCYYAATAAXXGCATTCXX-3',
``` wherein X and Y are any pair of natural or artificial nucleotides which can hybridize to each other.

20. The method of claim 1, wherein the probe (A) comprises a nucleic acid sequence selected from the group consisting of:

```
                                     (SEQ ID NO: 29)
5'-P-GAGGXX-Z-YYCCTCAGCYYAATAAXXGCT-3', (SEQ ID NO: 30)
5'-P-CAGCXX-Z-YYGCTGAGGYYAATAAXXCCT-3', (SEQ ID NO: 31)
5'-P-XXGATCCXX-Z-YYGGATCYYYYYYYAATAAXXXXX-3',
and (SEQ ID NO: 32)
5'-P-TTCYY-Z-XXGAATGCYYAATAAXXGCA-3'
``` wherein
Z is the one or more oligonucleotides to be amplified,
X and Y are any pair of natural or artificial nucleotides which can hybridize to each other, and
P is a 5'-phosphate.

21. The method of claim 1, wherein the probe (A) is created by ligation of one or more nucleic acid sequences comprising one or more parts of the one or more oligonucleotides and the one or more nicking cassettes.

22. The method of claim 1, wherein the one or more double stranded nicking cassettes further comprise a recognition site for a restriction endonuclease capable of recognising said recognition site and cleaving both of said strands.

23. The method of claim 22, wherein steps b) to i) are performed one or more times.

24. The method of claim 1, wherein probe (A) is obtained after step h) by cleaving the rolling circle product of probe (B) with the restriction enzyme.

25. The method of claim 1, wherein probe (B) is obtained after step d) by cleaving the rolling circle product of probe (A) with the restriction enzyme.

26. The method of claim 24, wherein the restriction endonuclease cleaves the double stranded nucleic acid either within a nucleic acid sequence of the one or more nicking cassettes or at the border of the one or more nicking cassettes and the one or more oligonucleotides.

27. The method of claim 24, wherein the restriction endonuclease is a type IIS restriction enzyme.

28. The method of claim 24, wherein the restriction endonuclease is the restriction enzyme Mly I.

29. The method of claim 22, wherein the one or more nicking cassettes comprise the complementary sequences:

```
5'-XXCCTCAGCGAGTCXXXXX-3'            (SEQ ID NO: 34)
and

5'-YYYYYGACTCGCTGAGGYY-3',           (SEQ ID NO: 35)
``` wherein X and Y are any natural or artificial nucleotide which can hybridize to each other.

30. The method of claim 22, wherein the one or more nicking cassettes comprise the complementary sequences:

```
5'-XCCTCAGCGAGTCXXXXX-3'             (SEQ ID NO: 36)
and

5'-YYYYYGACTCGCTGAGGY-3',            (SEQ ID NO: 37)
``` wherein X and Y are any pair of natural or artificial nucleotides which can hybridize to each other.

31. The method of claim 22, wherein the one or more nicking cassettes comprise the complementary sequences:

```
5'-XXGAGTCGATCC-3'                   (SEQ ID NO: 38)
and

5'-GGATCGACTCYY-3',                  (SEQ ID NO: 39)
``` wherein X and Y are any pair of natural or artificial nucleotides which can hybridize to each other.

32. The method of claim 22, wherein the one or more nicking cassettes comprise a nucleic acid sequence selected from the group consisting of:

```
                                     (SEQ ID NO: 40)
5'-GGATCGACTCYYAATAAXXGAGTCGATCC-3', (SEQ ID NO: 6)
5'-GGATCGACTCAAAATAATTGAGTCGATCC-3', (SEQ ID NO: 41)
```

-continued

```
5'-GGATCGACTCGCTGAGGYYAATAAXXCCTCAGCGAGTCGATCC-3',
and
                                          (SEQ ID NO: 7)
5'-GGATCGACTCGCTGAGGAAAATAATTCCTCAGCGAGTCGATCC-3'
``` wherein X and Y are any pair of natural or artificial nucleotides which can hybridize to each other.

33. The method of claim 22, wherein the probe (A) comprises a nucleic acid sequence selected from the group consisting of:

```
                                         (SEQ ID NO: 42)
   5'-P-TCGATCC-Z-GGATCGACTCYYAATAAXXGAG-3', (SEQ ID NO: 43)
   5'-P-TCGATCC-Z-GGATCGACTCAAAATAATTGAG-3', (SEQ ID NO: 44)
   5'-P-CGAGTCGATCC-Z-
   GGATCGACTCGCTGAGGYYAATAAXXCCTCAG-3',
   and (SEQ ID NO: 45)
   5'-P-CGAGTCGATCC-Z-
   GGATCGACTCGCTGAGGAAAATAATTCCTCAG-3'
``` wherein
Z is the one or more oligonucleotides to be amplified,
X and Y are any pair of natural or artificial nucleotides which can hybridize to
each other,
P is a 5'-phosphate.

34. A circular nucleic acid probe comprising more than one single stranded oligonucleotide covalently linked to one or more double stranded nicking cassette(s) having complementary sequences,
each nicking cassette comprising a double stranded nicking endonuclease recognition site having complementary nucleic acid sequences, wherein a nicking endonuclease capable of recognising said double stranded recognition site generates a nick in only one of the strands of the double stranded nucleic acid, and
each nicking cassette further comprising a double stranded restriction endonuclease recognition site having complementary nucleic acid sequences, wherein a restriction endonuclease capable of recognising said double stranded recognition site generates a nick in both of the strands of the double stranded nucleic acid wherein either (i) the one or more nicking cassettes comprise a nucleic acid sequence selected from the group consisting of:

```
                                         (SEQ ID NO: 25)
   5'-YYCCTCAGCYYAATAAXXGCTGAGGXX-3', (SEQ ID NO: 26)
   5'-YYGCTGAGGYYAATAAXXCCTCAGCXX-3', (SEQ ID NO: 27)
   5'-YYGGATCYYYYYYYAATAAXXXXXXXGATCCXX-3',
   and (SEQ ID NO: 28)
   5'-YYGAATGCYYAATAAXXGCATTCXX-3'
``` wherein X and Y are any pair of natural or artificial nucleotides which can hybridize to each other;
or wherein (ii) the probe comprises a nucleic acid sequence selected from the group consisting of:

```
                                         (SEQ ID NO: 29)
   5'-P-GAGGXX-Z-YYCCTCAGCYYAATAAXXGCT-3', (SEQ ID NO: 30)
   5'-P-CAGCXX-Z-YYGCTGAGGYYAATAAXXCCT-3', (SEQ ID NO: 31)
   5'-P-XXGATCCXX-Z-YYGGATCYYYYYYYAATAAXXXXX-3',
   and (SEQ ID NO: 32)
   5'-P-TTCYY-Z-XXGAATGCYYAATAAXXGCA-3'
``` wherein
Z is the one or more oligonucleotides to be amplified,
X and Y are any pair of natural or artificial nucleotides which can hybridize to
each other, and
P is a 5'-phosphate.

35. The circularised nucleic acid probe according to claim 34, wherein the one or more oligonucleotides comprise a sequence of from 10 to 1000 nucleotides.

36. The circularised nucleic acid probe according to claim 34, wherein the one or more nicking cassettes have a length of from 20 to 200 nucleotides.

37. The circularised nucleic acid probe according to claim 34, wherein the one or more nicking cassettes comprise a nucleic acid sequence selected from the group consisting of:

```
                                         (SEQ ID NO: 25)
   5'-YYCCTCAGCYYAATAAXXGCTGAGGXX-3', (SEQ ID NO: 26)
   5'-YYGCTGAGGYYAATAAXXCCTCAGCXX-3', (SEQ ID NO: 27)
   5'-YYGGATCYYYYYYYAATAAXXXXXXXGATCCXX-3',
   and (SEQ ID NO: 28)
   5'-YYGAATGCYYAATAAXXGCATTCXX-3'
``` wherein X and Y are any pair of natural or artificial nucleotides which can hybridize to each other.

38. The circularised nucleic acid probe according to claim 34, wherein the probe comprises a nucleic acid sequence selected from the group consisting of:

```
                                         (SEQ ID NO: 29)
   5'-P-GAGGXX-Z-YYCCTCAGCYYAATAAXXGCT-3', (SEQ ID NO: 30)
   5'-P-CAGCXX-Z-YYGCTGAGGYYAATAAXXCCT-3', (SEQ ID NO: 31)
   5'-P-XXGATCCXX-Z-YYGGATCYYYYYYYAATAAXXXXX-3',
   and (SEQ ID NO: 32)
   5'-P-TTCYY-Z-XXGAATGCYYAATAAXXGCA-3'
``` wherein
Z is the one or more oligonucleotides to be amplified,
X and Y are any pair of natural or artificial nucleotides which can hybridize to
each other,
P is a 5'-phosphate.

39. The circularised nucleic acid probe according to claim 34, wherein the nicking endonuclease recognition site is recognised by a nicking endonuclease selected from the group consisting of N.Alw I (Nt.Alw I), N.BbvC IA (Nb.BbvC I), N.BbvC IB (Nt.BbvC I), Nt.BstNB I, Nb.BpulOI and Nb.Bsm I.

40. The circularised nucleic acid probe according to claim 34, wherein the restriction endonuclease recognition site is recognised by a restriction endonuclease of tune IIS.

41. The circularised nucleic acid probe according to claim 40, wherein the restriction endonuclease is Mly I.

* * * * *

UNITED STATES PATENT AND TRADEMARK OFFICE
CERTIFICATE OF CORRECTION

| | | |
|---|---|---|
| PATENT NO. | : 8,080,393 B2 | Page 1 of 1 |
| APPLICATION NO. | : 11/911521 | |
| DATED | : December 20, 2011 | |
| INVENTOR(S) | : Jorn E. Koch et al. | |

It is certified that error appears in the above-identified patent and that said Letters Patent is hereby corrected as shown below:

In the Claims:

In Col. 67, line 7
replace "of tune IIS"
with "of type IIS"

Signed and Sealed this
First Day of July, 2014

Michelle K. Lee
*Deputy Director of the United States Patent and Trademark Office*

SEQUENCE LISTING

```
<160> NUMBER OF SEQ ID NOS: 48

<210> SEQ ID NO 1
<211> LENGTH: 92
<212> TYPE: DNA
<213> ORGANISM: Artificial Sequence
<220> FEATURE:
<223> OTHER INFORMATION: Synthetic rolling circle template

<400> SEQUENCE: 1
gtcgatcccc tcaatgctgc tgctgtacta cgcatgtgtg agccgagtcc tgggtgcacg      60
tcccacagct cggatcgact cggaataacc ga                                    92

<210> SEQ ID NO 2
<211> LENGTH: 85
<212> TYPE: DNA
<213> ORGANISM: Artificial Sequence
<220> FEATURE:
<223> OTHER INFORMATION: Synthetic rolling circle template

<400> SEQUENCE: 2
gtcgatcccc tcaatgcaca tgtttggctc caaaatagc ggacaagccg aatacccttc       60
tcccggatcg actcggaata accga                                            85

<210> SEQ ID NO 3
<211> LENGTH: 84
<212> TYPE: DNA
<213> ORGANISM: Artificial Sequence
<220> FEATURE:
<223> OTHER INFORMATION: Synthetic rolling circle template

<400> SEQUENCE: 3
gtcgatcccc tcaatgctgc tgctgtacta caaaacatgc ggaccaccag ctggtacttg      60
accggatcga ctcggaataa ccga                                             84
```

```
<210> SEQ ID NO 4
<211> LENGTH: 85
<212> TYPE: DNA
<213> ORGANISM: Artificial Sequence
<220> FEATURE:
<223> OTHER INFORMATION: Synthetic rolling circle template

<400> SEQUENCE: 4
gtcgatcccc tcaatgctgc tgctgtacta caaaaatagc ggacaagccg aatacccttc      60
tcccggatcg actcggaata accga                                            85

<210> SEQ ID NO 5
<211> LENGTH: 92
<212> TYPE: DNA
<213> ORGANISM: Artificial Sequence
<220> FEATURE:
<223> OTHER INFORMATION: Synthetic rolling circle template

<400> SEQUENCE: 5
gtcgatcccc tcaatgctgc tgctgtacta cgcatgtgtg agccgagtcc tgggtgcacg      60
tcccacagct cggatcgact cggaataacc ga                                    92

<210> SEQ ID NO 6
<211> LENGTH: 29
<212> TYPE: DNA
<213> ORGANISM: Artificial Sequence
<220> FEATURE:
<223> OTHER INFORMATION: Synthetic suicide cassette

<400> SEQUENCE: 6
ggatcgactc aaaataattg agtcgatcc                                        29

<210> SEQ ID NO 7
<211> LENGTH: 43
<212> TYPE: DNA
<213> ORGANISM: Artificial Sequence
<220> FEATURE:
<223> OTHER INFORMATION: Synthetic suicide cassette

<400> SEQUENCE: 7
ggatcgactc gctgaggaaa ataattcctc agcgagtcga tcc                        43

<210> SEQ ID NO 8
<211> LENGTH: 98
<212> TYPE: DNA
<213> ORGANISM: Artificial Sequence
<220> FEATURE:
<223> OTHER INFORMATION: Synthetic probe

<400> SEQUENCE: 8
gtcgatccct gccatcttaa caaaccctcg acctcaatgc tgctgctgta ctactcttat      60
gcgattaccg ggctggatcg actcggaatt tcttccga                              98

<210> SEQ ID NO 9
<211> LENGTH: 23
<212> TYPE: DNA
<213> ORGANISM: Artificial Sequence
<220> FEATURE:
<223> OTHER INFORMATION: Synthetic primer

<400> SEQUENCE: 9
gtagtacagc agcagcattg agg                                              23

<210> SEQ ID NO 10
<211> LENGTH: 23
```

```
<212> TYPE: DNA
<213> ORGANISM: Artificial Sequence
<220> FEATURE:
<223> OTHER INFORMATION: Synthetic primer

<400> SEQUENCE: 10
cctcaatgct gctgctgtac tac                                          23

<210> SEQ ID NO 11
<211> LENGTH: 66
<212> TYPE: DNA
<213> ORGANISM: Artificial Sequence
<220> FEATURE:
<223> OTHER INFORMATION: Synthetic oligonucleotide to be amplified

<400> SEQUENCE: 11
ctgccatctt aacaaaccct cgacctcaat gctgctgctg tactactctt atgcgattac    60
cgggct                                                             66

<210> SEQ ID NO 12
<211> LENGTH: 17
<212> TYPE: DNA
<213> ORGANISM: Artificial Sequence
<220> FEATURE:
<223> OTHER INFORMATION: Synthetic cleavage oligonucleotide

<400> SEQUENCE: 12
gtttgttaag atggcag                                                 17

<210> SEQ ID NO 13
<211> LENGTH: 17
<212> TYPE: DNA
<213> ORGANISM: Artificial Sequence
<220> FEATURE:
<223> OTHER INFORMATION: Synthetic cleavage oligonucleotide

<400> SEQUENCE: 13
ctgccatctt aacaaac                                                 17

<210> SEQ ID NO 14
<211> LENGTH: 10
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (6)..(10)
<223> OTHER INFORMATION: n is a, c, g, t, unknown or other nucleotide

<400> SEQUENCE: 14 gagtcnnnnn                                                         10

<210> SEQ ID NO 15
<211> LENGTH: 10
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (6)..(10)
<223> OTHER INFORMATION: n is a, c, g, t, unknown or other nucleotide

<400> SEQUENCE: 15 ggatcnnnnn                                                         10
```

```
<210> SEQ ID NO 16
<211> LENGTH: 10
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (6)..(10)
<223> OTHER INFORMATION: n is a, c, g, t, unknown or other nucleotide
<220> FEATURE:
<221> NAME/KEY: misc_feature
<222> LOCATION: (9)..(10)
<223> OTHER INFORMATION: Nicking enzyme nicks the recognition sequence
      between these two nucleotides

<400> SEQUENCE: 16 ggatcnnnnn                                                          10

<210> SEQ ID NO 17
<211> LENGTH: 11
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(2)
<223> OTHER INFORMATION: n is a, c, g, t, unknown or other nucleotide
<220> FEATURE:
<221> NAME/KEY: misc_feature
<222> LOCATION: (10)..(11)
<223> OTHER INFORMATION: n is a, c, g, t, unknown or other nucleotide

<400> SEQUENCE: 17
nngctgaggn n                                                        11

<210> SEQ ID NO 18
<211> LENGTH: 11
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(2)
<223> OTHER INFORMATION: n is a, c, g, t, unknown or other nucleotide
<220> FEATURE:
<221> NAME/KEY: misc_feature
<222> LOCATION: (10)..(11)
<223> OTHER INFORMATION: n is a, c, g, t, unknown or other nucleotide

<400> SEQUENCE: 18
nncctcagcn n                                                        11

<210> SEQ ID NO 19
<211> LENGTH: 11
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(2)
<223> OTHER INFORMATION: n is a, c, g, t, unknown or other nucleotide
<220> FEATURE:
<221> NAME/KEY: misc_feature
<222> LOCATION: (10)..(11)
<223> OTHER INFORMATION: n is a, c, g, t, unknown or other nucleotide

<400> SEQUENCE: 19
nncctcagcn n                                                        11
```

```
<210> SEQ ID NO 20
<211> LENGTH: 11
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(2)
<223> OTHER INFORMATION: n is a, c, g, t, unknown or other nucleotide
<220> FEATURE:
<221> NAME/KEY: misc_feature
<222> LOCATION: (10)..(11)
<223> OTHER INFORMATION: n is a, c, g, t, unknown or other nucleotide

<400> SEQUENCE: 20
nngctgaggn n                                                          11

<210> SEQ ID NO 21
<211> LENGTH: 14
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(7)
<223> OTHER INFORMATION: n is a, c, g, t, unknown or other nucleotide
<220> FEATURE:
<221> NAME/KEY: misc_feature
<222> LOCATION: (13)..(14)
<223> OTHER INFORMATION: n is a, c, g, t, unknown or other nucleotide

<400> SEQUENCE: 21
nnnnnnngat ccnn                                                       14

<210> SEQ ID NO 22
<211> LENGTH: 14
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(2)
<223> OTHER INFORMATION: n is a, c, g, t, unknown or other nucleotide
<220> FEATURE:
<221> NAME/KEY: misc_feature
<222> LOCATION: (8)..(14)
<223> OTHER INFORMATION: n is a, c, g, t, unknown or other nucleotide

<400> SEQUENCE: 22
nnggatcnnn nnnn                                                       14

<210> SEQ ID NO 23
<211> LENGTH: 10
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(2)
<223> OTHER INFORMATION: n is a, c, g, t, unknown or other nucleotide
<220> FEATURE:
<221> NAME/KEY: misc_feature
<222> LOCATION: (9)..(10)
<223> OTHER INFORMATION: n is a, c, g, t, unknown or other nucleotide

<400> SEQUENCE: 23 nngaatgcnn                                                            10
```

```
<210> SEQ ID NO 24
<211> LENGTH: 10
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(2)
<223> OTHER INFORMATION: n is a, c, g, t, unknown or other nucleotide
<220> FEATURE:
<221> NAME/KEY: misc_feature
<222> LOCATION: (9)..(10)
<223> OTHER INFORMATION: n is a, c, g, t, unknown or other nucleotide

<400> SEQUENCE: 24 nngcattcnn                                                              10

<210> SEQ ID NO 25
<211> LENGTH: 27
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(2)
<223> OTHER INFORMATION: n is a, c, g, t, unknown or other nucleotide
<220> FEATURE:
<221> NAME/KEY: misc_feature
<222> LOCATION: (10)..(11)
<223> OTHER INFORMATION: n is a, c, g, t, unknown or other nucleotide
<220> FEATURE:
<221> NAME/KEY: misc_feature
<222> LOCATION: (17)..(18)
<223> OTHER INFORMATION: n is a, c, g, t, unknown or other nucleotide
<220> FEATURE:
<221> NAME/KEY: misc_feature
<222> LOCATION: (26)..(27)
<223> OTHER INFORMATION: n is a, c, g, t, unknown or other nucleotide

<400> SEQUENCE: 25
nncctcagcn naataanngc tgaggnn                                           27

<210> SEQ ID NO 26
<211> LENGTH: 27
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(2)
<223> OTHER INFORMATION: n is a, c, g, t, unknown or other nucleotide
<220> FEATURE:
<221> NAME/KEY: misc_feature
<222> LOCATION: (10)..(11)
<223> OTHER INFORMATION: n is a, c, g, t, unknown or other nucleotide
<220> FEATURE:
<221> NAME/KEY: misc_feature
<222> LOCATION: (17)..(18)
<223> OTHER INFORMATION: n is a, c, g, t, unknown or other nucleotide
<220> FEATURE:
<221> NAME/KEY: misc_feature
<222> LOCATION: (26)..(27)
<223> OTHER INFORMATION: n is a, c, g, t, unknown or other nucleotide

<400> SEQUENCE: 26
nngctgaggn naataanncc tcagcnn                                           27

<210> SEQ ID NO 27
<211> LENGTH: 33
<212> TYPE: DNA
```

```
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(2)
<223> OTHER INFORMATION: n is a, c, g, t, unknown or other nucleotide
<220> FEATURE:
<221> NAME/KEY: misc_feature
<222> LOCATION: (8)..(14)
<223> OTHER INFORMATION: n is a, c, g, t, unknown or other nucleotide
<220> FEATURE:
<221> NAME/KEY: misc_feature
<222> LOCATION: (20)..(26)
<223> OTHER INFORMATION: n is a, c, g, t, unknown or other nucleotide
<220> FEATURE:
<221> NAME/KEY: misc_feature
<222> LOCATION: (32)..(33)
<223> OTHER INFORMATION: n is a, c, g, t, unknown or other nucleotide

<400> SEQUENCE: 27
nnggatcnnn nnnnaataan nnnnnngatc cnn                                    33

<210> SEQ ID NO 28
<211> LENGTH: 25
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(2)
<223> OTHER INFORMATION: n is a, c, g, t, unknown or other nucleotide
<220> FEATURE:
<221> NAME/KEY: misc_feature
<222> LOCATION: (9)..(10)
<223> OTHER INFORMATION: n is a, c, g, t, unknown or other nucleotide
<220> FEATURE:
<221> NAME/KEY: misc_feature
<222> LOCATION: (16)..(17)
<223> OTHER INFORMATION: n is a, c, g, t, unknown or other nucleotide
<220> FEATURE:
<221> NAME/KEY: misc_feature
<222> LOCATION: (24)..(25)
<223> OTHER INFORMATION: n is a, c, g, t, unknown or other nucleotide

<400> SEQUENCE: 28
nngaatgcnn aataanngca ttcnn                                             25

<210> SEQ ID NO 29
<211> LENGTH: 28
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: Preceded by 5'-phosphate
<220> FEATURE:
<221> NAME/KEY: misc_feature
<222> LOCATION: (1)..(28)
<223> OTHER INFORMATION: n is a, c, g, t, unknown or other nucleotide
<220> FEATURE:
<221> NAME/KEY: misc_feature
<222> LOCATION: (7)..(7)
<223> OTHER INFORMATION: amplification site

<400> SEQUENCE: 29
gaggnnnnnc ctcagcnnaa taanngct                                          28

<210> SEQ ID NO 30
<211> LENGTH: 28
<212> TYPE: DNA
```

```
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: Preceded by 5'-phosphate
<220> FEATURE:
<221> NAME/KEY: misc_feature
<222> LOCATION: (1)..(28)
<223> OTHER INFORMATION: n is a, c, g, t, unknown or other nucleotide
<220> FEATURE:
<221> NAME/KEY: misc_feature
<222> LOCATION: (7)..(7)
<223> OTHER INFORMATION: amplification site

<400> SEQUENCE: 30 cagcnnnng ctgaggnnaa taanncct                                           28

<210> SEQ ID NO 31
<211> LENGTH: 34
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: Preceded by 5'-phosphate
<220> FEATURE:
<221> NAME/KEY: misc_feature
<222> LOCATION: (1)..(34)
<223> OTHER INFORMATION: n is a, c, g, t, unknown or other nucleotide
<220> FEATURE:
<221> NAME/KEY: misc_feature
<222> LOCATION: (10)..(10)
<223> OTHER INFORMATION: amplification site

<400> SEQUENCE: 31
nngatccnnn nnggatcnnn nnnnaataan nnnn                                   34

<210> SEQ ID NO 32
<211> LENGTH: 26
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: Preceded by 5'-phosphate
<220> FEATURE:
<221> NAME/KEY: misc_feature
<222> LOCATION: (1)..(26)
<223> OTHER INFORMATION: n is a, c, g, t, unknown or other nucleotide
<220> FEATURE:
<221> NAME/KEY: misc_feature
<222> LOCATION: (6)..(6)
<223> OTHER INFORMATION: amplification site

<400> SEQUENCE: 32
ttcnnnnnga atgcnnaata anngca                                            26

<210> SEQ ID NO 33
<211> LENGTH: 26
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: Preceded by 5'-phosphate
<220> FEATURE:
```

<221> NAME/KEY: misc_feature
<222> LOCATION: (1)..(26)
<223> OTHER INFORMATION: n is a, c, g, t, unknown or other nucleotide
<220> FEATURE:
<221> NAME/KEY: misc_feature
<222> LOCATION: (6)..(6)
<223> OTHER INFORMATION: amplification site

<400> SEQUENCE: 33
ttcnnnnnga atgcnnaata anngca                                          26

<210> SEQ ID NO 34
<211> LENGTH: 19
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(2)
<223> OTHER INFORMATION: n is a, c, g, t, unknown or other nucleotide
<220> FEATURE:
<221> NAME/KEY: misc_feature
<222> LOCATION: (15)..(19)
<223> OTHER INFORMATION: n is a, c, g, t, unknown or other nucleotide

<400> SEQUENCE: 34
nncctcagcg agtcnnnnn                                                  19

<210> SEQ ID NO 35
<211> LENGTH: 19
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(5)
<223> OTHER INFORMATION: n is a, c, g, t, unknown or other nucleotide
<220> FEATURE:
<221> NAME/KEY: misc_feature
<222> LOCATION: (18)..(19)
<223> OTHER INFORMATION: n is a, c, g, t, unknown or other nucleotide

<400> SEQUENCE: 35
nnnnngactc gctgaggnn                                                  19

<210> SEQ ID NO 36
<211> LENGTH: 18
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: n is a, c, g, t, unknown or other nucleotide
<220> FEATURE:
<221> NAME/KEY: misc_feature
<222> LOCATION: (14)..(18)
<223> OTHER INFORMATION: n is a, c, g, t, unknown or other nucleotide

<400> SEQUENCE: 36
ncctcagcga gtcnnnnn                                                   18

<210> SEQ ID NO 37
<211> LENGTH: 18
<212> TYPE: DNA
<213> ORGANISM: Artificial Sequence
<220> FEATURE:
<223> OTHER INFORMATION: Synthetic oligonucleotide
<220> FEATURE:

```
<221> NAME/KEY: misc_feature
<222> LOCATION: (1)..(5)
<223> OTHER INFORMATION: n is a, c, g, t, unknown or other nucleotide
<220> FEATURE:
<221> NAME/KEY: misc_feature
<222> LOCATION: (18)..(18)
<223> OTHER INFORMATION: n is a, c, g, t, unknown or other nucleotide

<400> SEQUENCE: 37
nnnnngactc gctgaggn                                                  18

<210> SEQ ID NO 38
<211> LENGTH: 12
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(2)
<223> OTHER INFORMATION: n is a, c, g, t, unknown or other nucleotide

<400> SEQUENCE: 38
nngagtcgat cc                                                        12

<210> SEQ ID NO 39
<211> LENGTH: 12
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (11)..(12)
<223> OTHER INFORMATION: n is a, c, g, t, unknown or other nucleotide

<400> SEQUENCE: 39
ggatcgactc nn                                                        12

<210> SEQ ID NO 40
<211> LENGTH: 29
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (11)..(12)
<223> OTHER INFORMATION: n is a, c, g, t, unknown or other nucleotide
<220> FEATURE:
<221> NAME/KEY: misc_feature
<222> LOCATION: (18)..(19)
<223> OTHER INFORMATION: n is a, c, g, t, unknown or other nucleotide

<400> SEQUENCE: 40
ggatcgactc nnaataanng agtcgatcc                                      29

<210> SEQ ID NO 41
<211> LENGTH: 43
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (18)..(19)
<223> OTHER INFORMATION: n is a, c, g, t, unknown or other nucleotide
<220> FEATURE:
<221> NAME/KEY: misc_feature
<222> LOCATION: (25)..(26)
<223> OTHER INFORMATION: n is a, c, g, t, unknown or other nucleotide
```

```
<400> SEQUENCE: 41
ggatcgactc gctgaggnna ataanncctc agcgagtcga tcc                    43

<210> SEQ ID NO 42
<211> LENGTH: 30
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: Preceded by 5'-phosphate
<220> FEATURE:
<221> NAME/KEY: misc_feature
<222> LOCATION: (1)..(30)
<223> OTHER INFORMATION: n is a, c, g, t, unknown or other nucleotide
<220> FEATURE:
<221> NAME/KEY: misc_feature
<222> LOCATION: (8)..(8)
<223> OTHER INFORMATION: amplification site

<400> SEQUENCE: 42
tcgatccngg atcgactcnn aataanngag                                   30

<210> SEQ ID NO 43
<211> LENGTH: 30
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: Preceded by 5'-phosphate
<220> FEATURE:
<221> NAME/KEY: misc_feature
<222> LOCATION: (1)..(30)
<223> OTHER INFORMATION: n is a, c, g, t, unknown or other nucleotide
<220> FEATURE:
<221> NAME/KEY: misc_feature
<222> LOCATION: (8)..(8)
<223> OTHER INFORMATION: amplification site

<400> SEQUENCE: 43
tcgatccngg atcgactcaa ataattgag                                    30

<210> SEQ ID NO 44
<211> LENGTH: 44
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: Preceded by 5'-phosphate
<220> FEATURE:
<221> NAME/KEY: misc_feature
<222> LOCATION: (1)..(44)
<223> OTHER INFORMATION: n is a, c, g, t, unknown or other nucleotide
<220> FEATURE:
<221> NAME/KEY: misc_feature
<222> LOCATION: (12)..(12)
<223> OTHER INFORMATION: amplification site

<400> SEQUENCE: 44
cgagtcgatc cnggatcgac tcgctgaggn naataanncc tcag                   44

<210> SEQ ID NO 45
<211> LENGTH: 44
<212> TYPE: DNA
```

```
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: Preceded by 5'-phosphate
<220> FEATURE:
<221> NAME/KEY: misc_feature
<222> LOCATION: (1)..(44)
<223> OTHER INFORMATION: n is a, c, g, t, unknown or other nucleotide
<220> FEATURE:
<221> NAME/KEY: misc_feature
<222> LOCATION: (12)..(12)
<223> OTHER INFORMATION: amplification site

<400> SEQUENCE: 45
cgagtcgatc cnggatcgac tcgctgagga aaataattcc tcag              44

<210> SEQ ID NO 46
<211> LENGTH: 11
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(2)
<223> OTHER INFORMATION: n is a, c, g, t, unknown or other nucleotide
<220> FEATURE:
<221> NAME/KEY: misc_feature
<222> LOCATION: (9)..(11)
<223> OTHER INFORMATION: n is a, c, g, t, unknown or other nucleotide

<400> SEQUENCE: 46
nngaatgcnn n                                                  11

<210> SEQ ID NO 47
<211> LENGTH: 25
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(2)
<223> OTHER INFORMATION: n is a, c, g, t, unknown or other nucleotide
<220> FEATURE:
<221> NAME/KEY: misc_feature
<222> LOCATION: (9)..(10)
<223> OTHER INFORMATION: n is a, c, g, t, unknown or other nucleotide
<220> FEATURE:
<221> NAME/KEY: misc_feature
<222> LOCATION: (16)..(17)
<223> OTHER INFORMATION: n is a, c, g, t, unknown or other nucleotide
<220> FEATURE:
<221> NAME/KEY: misc_feature
<222> LOCATION: (24)..(25)
<223> OTHER INFORMATION: n is a, c, g, t, unknown or other nucleotide

<400> SEQUENCE: 47
nngaatgcnn aataanngca ttgnn                                   25

<210> SEQ ID NO 48
<211> LENGTH: 43
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(5)
<223> OTHER INFORMATION: n is a, c, g, t, unknown or other nucleotide
<220> FEATURE:
```

```
<221> NAME/KEY: misc_feature
<222> LOCATION: (18)..(19)
<223> OTHER INFORMATION: n is a, c, g, t, unknown or other nucleotide
<220> FEATURE:
<221> NAME/KEY: misc_feature
<222> LOCATION: (25)..(26)
<223> OTHER INFORMATION: n is a, c, g, t, unknown or other nucleotide
<220> FEATURE:
<221> NAME/KEY: misc_feature
<222> LOCATION: (39)..(43)
<223> OTHER INFORMATION: n is a, c, g, t, unknown or other nucleotide

<400> SEQUENCE: 48
nnnnngactc gctgaggnna ataanncctc agcgagtcnn nnn                    43
```